(12) United States Patent
Rice et al.

(10) Patent No.: US 9,139,829 B2
(45) Date of Patent: Sep. 22, 2015

(54) SIRNA TARGETING ETS1 AND ELK1 AND METHOD OF USING SAME IN THE INHIBITION OF CIP2A GENE IN CANCER TREATMENT

(71) Applicant: Medical Diagnostic Laboratories, LLC, Hamilton, NJ (US)

(72) Inventors: Lyndi M. Rice, Philadelphia, PA (US); Rajash Pallai, West Chester, PA (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 25 days.

(21) Appl. No.: 13/776,878

(22) Filed: Feb. 26, 2013

(65) Prior Publication Data
US 2013/0225657 A1 Aug. 29, 2013

Related U.S. Application Data

(60) Provisional application No. 61/722,386, filed on Nov. 5, 2012, provisional application No. 61/604,152, filed on Feb. 28, 2012.

(51) Int. Cl.
| | | |
|---|---|---|
| *C12N 15/11* | (2006.01) | |
| *C12N 15/113* | (2010.01) | |
| *A61K 31/713* | (2006.01) | |
| *C07K 14/82* | (2006.01) | |

(52) U.S. Cl.
CPC ............ *C12N 15/113* (2013.01); *A61K 31/713* (2013.01); *C07K 14/82* (2013.01); *C12N 2310/14* (2013.01); *C12N 2320/31* (2013.01)

(58) Field of Classification Search
CPC . C12N 15/113; C12N 2310/14; A61K 31/713
See application file for complete search history.

(56) References Cited

U.S. PATENT DOCUMENTS

2012/0156138 A1* 6/2012 Smith ............................ 424/9.2

OTHER PUBLICATIONS

Pallai et al. Transcription 3:323-335, 2012.*
Hoo, L.S., et al., Cloning and characterization of a novel 90kDa companion auto antigen of p62 overexpressed in cancer, Oncogene Jul. 25, 2002; 21 (32):5006-5015, Nature Publishing Group.
Li, W., et al., CIP2A is overexpressed in gastric cancer and its depletion leads to impaired clonogenicity, senescence or differentiation of tumor cells. Clinical Cancer Research Jun. 15, 2008; 14(12):3722-3728, American Association for Cancer Research.
Côme, C., et al., CIP2A is associated with human breast cancer aggressivity. Clinical Cancer Research Aug. 15, 2009; 15 (16) :5092-5100, American Association for Cancer Research.
Khanna, A., et al., MYC-dependent regulation and prognostic role of CIP2A in gastric cancer. Journal of National Cancer Institute Jun. 3, 2009; 101 (11)193-805, Oxford University Press.
Katz. J., et al., CIP2A expression and localization in oral carcinoma and dysplasia, Cancer Biology and Therapy Oct. 1, 2010; 10(7) :649-699.
Vaarala M., et al., CIP2A expression is increased in prostate cancer. Journal of Experimental Clinical Cancer Research Oct. 2010, 29:136.
Liu, J., et al., Cancerous inhibitor of protein phosphatase 2A is overexpressed in cervical cancer and upregulated by human pail-
lomavirus 16 E7 oncoprotein. Gynecologic Oncology Aug. 2011; 122(2): 430-436, Elsevier.
Qu, W., et al., CIP2A is overexpressed in esophageal squamous cell carcinoma. Medical Oncology Dec. 8, 2010; 29(1): 113-118, Springer Publishing.
Dong, Q.Z., et al., CIP2A is overexpressed in non-small cell lung cancer and correlates with poor prognosis, Annals of Surgical Oncology Sep. 15, 2011; 18(3): 857-865, The Society of Surgical Oncology.
Lucas C.M., et al., Cancerous inhibitor of PP2A (CIP2A) at diagnosis of chronic myeloid leukemia is a critical determinant of disease progression. Blood Jun. 2011, 117 24):6660-6668, American Society of Hematology.
Wang J., et al., CIP2A is over-expressed in acute myeloid leukemia and associated with HL60 cells proliferation and differentiation, International Journal Laboratory Hematology, Jun. 2011; 33(3): 290-298, John Wiley & Sons.
Lee J., et al.,CIP2A expression is associated with synoival hyperplasia and invasive function of fibroblast-like synoviocytes in rheumatioid arthritis, Rheumatology International, Apr. 9, 2011; 32(7):2023-2030, Springer Publishing.
Morel, A-P., et al., EMT Inducers Catalyze Malignant Transformation of Mammary Epithelial Cells and Drive Tumorigenesis towards Claudin-Low Tumors in Transgenic Mice, PLoS Genetics, May 24, 2012; 8(5):e1002723, Public Library of Science.
Zhang, W., et al.,PR55α a Regulatory Subunit of PP2A, Specifically Regulates PP2A-mediated β-Catenin Dephosphorylation, The Journal of Biological Chemistry, Aug. 21, 2009; 284(34) 22640-22656, American Society for Biochemistry and Molecular Biology.
Colas, E., et al.,The EMT signaling pathways in endometrial carcinoma, Clinical and Translational Oncology, Aug. 22, 2012; 14(10): 715-720, Springer Publishing.
Ortega-Gutiérrez, S., et al., Targeted Disruption of the PME-1 Gene Causes Loss of Demethylated PP2A and Perinatal Lethality in Mice, PLoS One, Jul. 2008, (3)7:e2486, Public Library of Science.
Ogris, E., et al., A Protein Phosphatase Methylesterase (PME-1) Is One of Several Novel Proteins Stably Associating with Two Inactive Mutants of Protein Phosphatase 2A, The Journal of Biological Chemistry 275(20):14382-14391, May 14, 1999; American Society for Biochemistry and Molecular Biology.
Bryant, J., et al., Methylated C-terminal leucine residue of PP2A catalytic subunit is important for binding of regulatory Bα subunit, Molecular Biology of the Cell, Jan. 2001, 12(1):185-199, American Society for Cell Biology.
Jackson, J., et al., Circumventing Cellular Control of PP2A by Methylation Promotes Transformation in an Akt-Dependent Manner, Neoplasia, Jul. 2012, 14(7): 585-599, Neoplasia Press.
Puustinen, P., et al., PME-1 protects ERK pathway actvity from protein phosphatase 2A-mediated inactivation in human malignant glioma, Cancer Research, Apr. 1, 2009; 69(7):2870-2877, American Association for Cancer Research.
Xing Xian, Y., et al., Methylation of the Protein Phosphatase 2A Catalytic Subunit But Not SG2NA, Striatin, or Polyomavirus Middle Tummor Antigen, vol. 12, 185-199, 2001.

* cited by examiner

*Primary Examiner* — Brian Whiteman
(74) *Attorney, Agent, or Firm* — Siu K. Lo

(57) ABSTRACT

Disclosed are methods of attenuating activity of the gene promoter of CIP2A. siRNAs are used to target against Ets1 and Elk1 transcriptional factors, thereby blocking the binding of Ets1 and Elk1 to the CIP2A gene promoter. It is disclosed that the siRNAs targeted against Ets1 and Elk1 attenuate the gene expression of CIP2A. A kit containing siRNA reagents for attenuating the CIP2A gene expression is also disclosed.

8 Claims, 31 Drawing Sheets

Figure 1    Putative Transcription Sites in CIP2A Promoter (~200 bp from ATG Transcription Start Site)

Transcription Sites:
1. Glucocorticoid receptor alpha (AATCA)
2. Retinoic acid receptor alpha (ACTTCCGGAG)
3. Pax5 (GGAGCCC)
4. Ets1 (CTTCCGG) ;(CCGGAAG)
5. Elk1 (CTTCCGGAG); (ATCCGGAAG)
6. NF-κB (GGGACTTCC)
7. Sp1 (TGGGCGGTGG)
8. AP-2 (CGGGCCGCGG)

Figure 4

**Nucleotide Sequence of CIP2A Promoter Fragment
(SEQ ID NO: 1)**

-2379 aaactggaaa ttaaaagcgt gagccactgc tcctggcctc ctgctcctttt tcttccctttt
ttgaggccta aaagtatgga ttggtgtttc tcaaattagg atatgcaagt atctctgatt
aaaaatgtca agacttatca cagctagaaa cgatccctct tactaaactt acaacatcaa
ttttggtgaa gatttttga gaaagacatt tgatattaat tacagaagag aatacaaaat
ttgtatgact gcttaagtca aaatccaaca aagatggcac tgatagcacg cagctttgcg
cattaccctg ggcctctgaa tggggacgat gctgacacat catcacagat gaaaagtcca
acactatcaa actctgatca cttcatttgc caatgaggca ctgactgtaa cactgagaac
ttaattatgc cagatgacag ctgacacttt acattaattc atttttttaac catctccaag
accgtatagg acctcatctc tactcctctc ctcctcgttc tttctacact agccacatgg
catccttgtt tctggcatac agtatcccac tttagggtct ttctttgcca tttcctctat
ctaaaaacct ttttcccatag aatatggctc cctttctcaa ctccttgaag catttcccca
aatgttgctt tctaatgag gtcaccttcc catttccctt atcaattacc aacattattc
tagagtaata acgtctattt ttctctttat atcattttcc ttacttattt attgtgttta
ttatttggtt ccctaccaaa atgtaagttg catgccagta gtattttgt tttttcact
gagtctattg tgtctagaaa agtgcttagc acattgtaga ttctcaatga actacttatt
gaatgaacag tcctatgaac caggtatctc ccttggccag attttaccta atgaagattc
tgcagcagtg agaacttgcc tagagtcaca tcgtcaaagg tggagctaga atctgtaagc
aacctggctc tctactcttt accactgctg catgttactg catggtgcct ctcatttatg
tggtgaattt caaaagtact attttgtatg tttcccttac tagacagttc cctcgcagca
ggggatacta cttcatctct gttccctgac tggcagtttc taacccatgt tacacgctct
ataattgttt acggaatgaa tgaaagcata aatgaacaca caagctaccc aaagattttt
acatgaatgt cccaactggt taaatcattt ttatctttca gatttaaact tttataaaaa
acaaaaccaa aacaccaaac ctgtcttcaa aaatctagta attcaaaaaa attcttttga
agtgaaaaaa catgatttct gataaacgat ttaattaaat ggaaatgtac cctattctta
caatttctac atcctggttt ttaaagcttt attcgacgtt aggaaatatt aagcaaaaag
ctccaaaacc agtaactgac tcgcttcatt acatacacat gcaataatat taagctatct
ccgatttaaa aaacgcaaat aatagtgcca ttttcgtaga catcgagaat tataaaacaa
tcaatcatgc cagagagaaa cagacacctt cacttacaaa aactgacgct aacgagtaac
accctccgga gcaatacctg gcccagggtc agcaggaggt agtcttctcg aataaatgtg
acaaatactt tggtcagggc atgactaatt tgccacataa tgccaatagg ttgactctga
gaaactacca tccccgggca gaaggggcgg gtgtaggaga gatttaaaaa cgaggcccct
cccaggccgc ctcaaaatct agggcccaag attcttctcc tcagagctcc tcaccgtgtc
tagactaggg gcaagcgacc atttctcagg tagaggatga cgcacaaacg aaaaactggc
catccaacat gaaggacgag gaagcgcacg aaatcagagc gcacagctga gtgaggaatc
cccccttctcc taaccgattc ctctcccgag aaatcgcgag atttctcgcc ttcacgggat
ctcaggccga aaacctcgcg gcctctcaga cgagggtggg ttagcggggg cagctcccaa
cccccgtcct ggacccacaa atcacctcga ccccctggccc acccccggccg tcaccgagaa
cggtccccta gggtgcctag ggacttccgg agcccgaccg gatccggaag cttctgagag
cgaggggggtg gggccgaaaa tcaaaaaaag cgcggcgaaa gctaaaggcc ggcgcacgct
gggcggtggt ggtccctaag ccgggccgcg gccggtgcaa tggactccac tgcctgcttg
aagtccttgc tcctgactgt cagtcagtac aaagccgtga agtcagagg +70

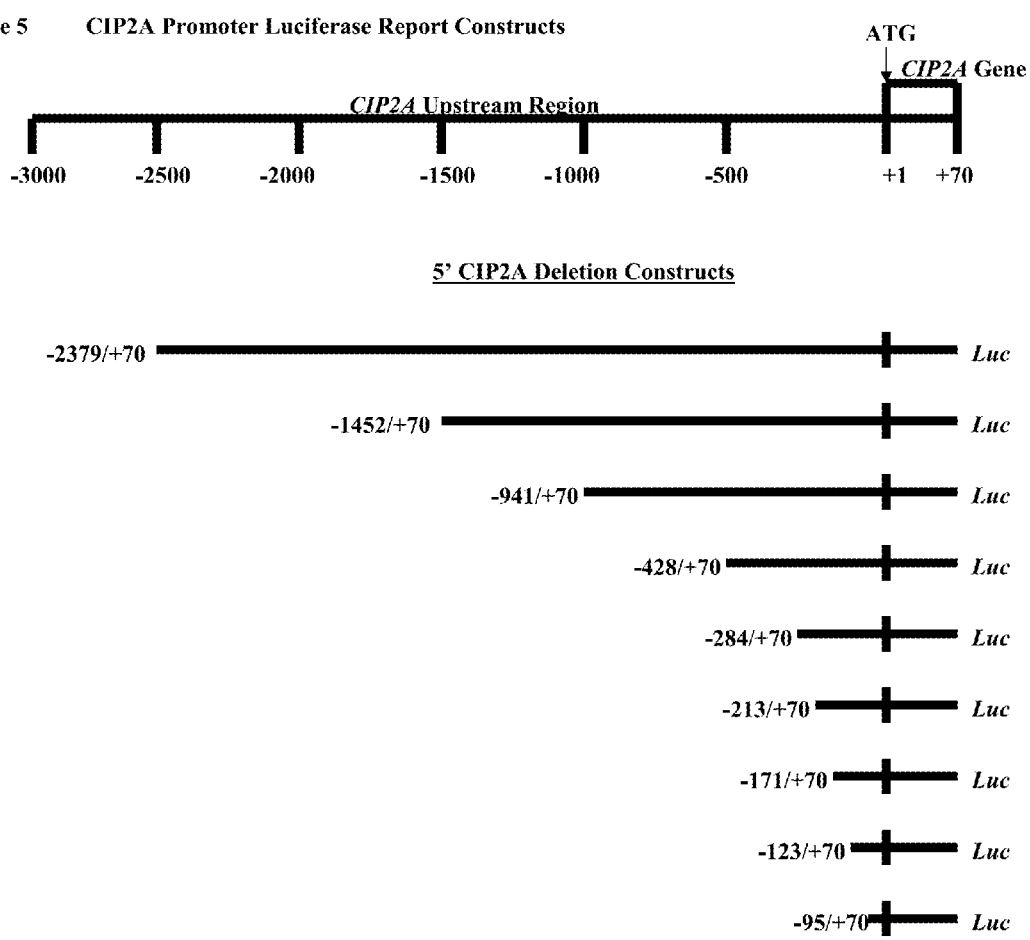
Figure 5  CIP2A Promoter Luciferase Report Constructs

Figure 16
A
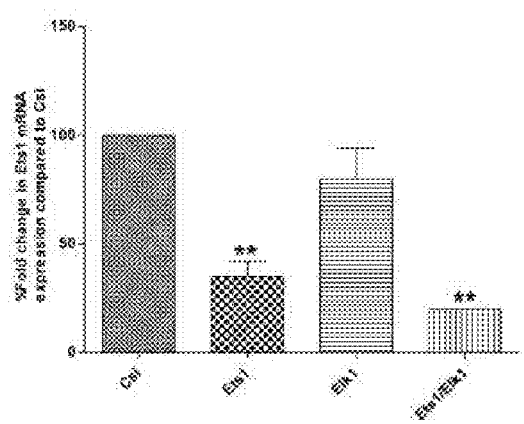
B
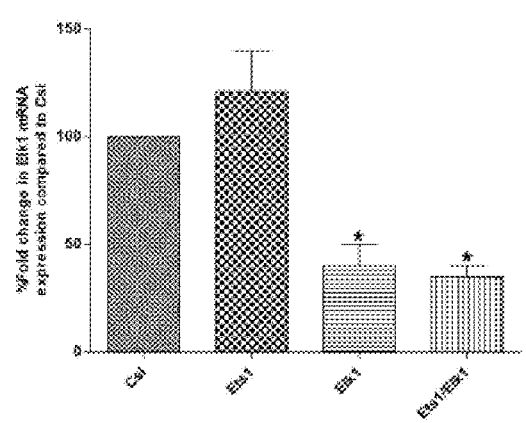

Figure 22

Nucleotide Sequence of A 5' CIP2A Promoter Deletion Construct Fragment (SEQ ID NO: 2)

-1452 ctcccttggc cagattttac ctaatgaaga ttctgcagca gtgagaactt gcctagagtc
acatcgtcaa aggtggagct agaatctgta agcaacctgg ctctctactc tttaccactg
ctgcatgtta ctgcatggtg cctctcattt atgtggtgaa tttcaaaagt actattttgt
atgtttccct tactagacag ttccctcgca gcaggggata ctacttcatc tctgttccct
gactggcagt ttctaaccca tgttacacgc tctataattg tttacggaat gaatgaaagc
ataaatgaac acacaagcta cccaaagatt tttacatgaa tgtcccaact ggttaaatca
tttttatctt tcagatttaa acttttataa aaaacaaaac caaaacacca aacctgtctt
caaaaatcta gtaattcaaa aaaattcttt tgaagtgaaa aaacatgatt tctgataaac
gatttaatta aatggaaatg taccctattc ttacaatttc tacatcctgg tttttaaagc
tttattcgac gttaggaaat attaagcaaa aagctccaaa accagtaact gactcgcttc
attacataca catgcaataa tattaagcta tctccgattt aaaaaacgca aataatagtg
ccatttcgt agacatcgag aattataaaa caatcaatca tgccagagag aaacagacac
cttcacttac aaaaactgac gctaacgagt aacaccctcc ggagcaatac ctggcccagg
gtcagcagga ggtagtcttc tcgaataaat gtgacaaata ctttggtcag ggcatgacta
atttgccaca taatgccaat aggttgactc tgagaaacta ccatccccgg gcagaagggg
cgggtgtagg agagatttaa aaacgaggcc cctcccaggc cgcctcaaaa tctagggccc
aagattcttc tcctcagagc tcctcaccgt gtctagacta ggggcaagcg accatttctc
aggtagagga tgacgcacaa acgaaaaact ggccatccaa catgaaggac gaggaagcgc
acgaaatcag agcgcacagc tgagtgagga atcccccttc tcctaaccga ttcctctccc
gagaaatcgc gagatttctc gccttcacgg gatctcaggc cgaaaacctc gcggcctctc
agacgagggt gggttagcgg gggcagctcc caaccccgt cctggaccca caaatcacct
cgacccctgg cccacccgg ccgtcaccga gaacggtccc ctagggtgcc tagggacttc
cggagcccga ccggatccgg aagcttctga gagcgagggg gtggggccga aaatcaaaaa
aagcgcggcg aaagctaaag gccggcgcac gctgggcggt ggtggtccct aagccgggcc
gcggccggtg caatggactc cactgcctgc ttgaagtcct tgctcctgac tgtcagtcag
tacaaagccg tgaagtcaga gg +70

Figure 23

Nucleotide Sequence of A 5' CIP2A Promoter Deletion Construct Fragment (SEQ ID NO: 3)

-941 tacaatttct acatcctggt ttttaaagct ttattcgacg ttaggaaata ttaagcaaaa
agctccaaaa ccagtaactg actcgcttca ttacatacac atgcaataat attaagctat
ctccgattta aaaaacgcaa ataatagtgc cattttcgta gacatcgaga attataaaac
aatcaatcat gccagagaga aacagacacc ttcacttaca aaaactgacg ctaacgagta
acaccctccg gagcaatacc tggcccaggg tcagcaggag gtagtcttct cgaataaatg
tgacaaatac tttggtcagg gcatgactaa tttgccacat aatgccaata ggttgactct
gagaaactac catccccggg cagaaggggc gggtgtagga gagatttaaa aacgaggccc
ctcccaggcc gcctcaaaat ctagggccca agattcttct cctcagagct cctcaccgtg
tctagactag gggcaagcga ccatttctca ggtagaggat gacgcacaaa cgaaaaactg
gccatccaac atgaaggacg aggaagcgca cgaaatcaga gcgcacagct gagtgaggaa
tccccttct cctaaccgat tcctctcccg agaaatcgcg agatttctcg ccttcacggg
atctcaggcc gaaaacctcg cggcctctca gacgagggtg ggttagcggg ggcagctccc
aaccccgtc ctggaccac aaatcacctc gaccctggc ccaccccggc cgtcaccgag
aacggtcccc tagggtgcct agggacttcc ggagcccgac cggatccgga agcttctgag
agcgaggggg tggggccgaa aatcaaaaaa agcgcggcga aagctaaagg ccggcgcacg
ctgggcggtg gtggtcccta agccgggccg cggccggtgc aatggactcc actgcctgct
tgaagtcctt gctcctgact gtcagtcagt acaaagccgt gaagtcagag g +70

Figure 24

Nucleotide Sequence of A 5' CIP2A Promoter Deletion Construct Fragment (SEQ ID NO: 4)

-428 agaggatgac gcacaaacga aaaactggcc atccaacatg aaggacgagg aagcgcacga
aatcagagcg cacagctgag tgaggaatcc cccttctcct aaccgattcc tctcccgaga
aatcgcgaga tttctcgcct tcacgggatc tcaggccgaa aacctcgcgg cctctcagac
gagggtgggt tagcgggggc agctcccaac ccccgtcctg gacccacaaa tcacctcgac
ccctggccca ccccggccgt caccgagaac ggtcccctag ggtgcctagg gacttccgga
gcccgaccgg atccggaagc ttctgagagc gaggggtgg ggccgaaaat caaaaaaagc
gcggcgaaag ctaaaggccg gcgcacgctg ggcggtggtg gtccctaagc cgggccgcgg
ccggtgcaat ggactccact gcctgcttga agtccttgct cctgactgtc agtcagtaca
aagccgtgaa gtcagagg +70

Figure 25

Nucleotide Sequence of A 5' CIP2A Promoter Deletion Construct Fragment (SEQ ID NO: 5)

-284 gggatctcag gccgaaaacc tcgcggcctc tcagacgagg gtgggttagc gggggcagct cccaaccccc gtcctggacc cacaaatcac ctcgacccct ggcccacccc ggccgtcacc gagaacggtc ccctagggtg cctagggact tccggagccc gaccggatcc ggaagcttct gagagcgagg gggtggggcc gaaaatcaaa aaaagcgcgg cgaaagctaa aggccggcgc acgctgggcg gtggtggtcc ctaagccggg ccgcggccgg tgcaatggac tccactgcct gcttgaagtc cttgctcctg actgtcagtc agtacaaagc cgtgaagtca gagg +70

Figure 26

Nucleotide Sequence of A 5' CIP2A Promoter Deletion Construct Fragment (SEQ ID NO: 6)

-213 tcctggaccc acaaatcacc tcgaccccctg gcccaccccg gccgtcaccg agaacggtcc
cctagggtgc ctagggactt ccggagcccg accggatccg gaagcttctg agagcgaggg
ggtggggccg aaaatcaaaa aaagcgcggc gaaagctaaa ggccggcgca cgctgggcgg
tggtggtccc taagccgggc cgcggccggt gcaatggact ccactgcctg cttgaagtcc
ttgctcctga ctgtcagtca gtacaaagcc gtgaagtcag agg +70

Figure 27

Nucleotide Sequence of A 5' CIP2A Promoter Deletion Construct Fragment (SEQ ID NO: 7)

-171 cgtcaccgag aacggtcccc tagggtgcct agggacttcc ggagcccgac cggatccgga
agcttctgag agcgaggggg tggggccgaa aatcaaaaaa agcgcggcga aagctaaagg
ccggcgcacg ctgggcggtg gtggtcccta agccgggccg cggccggtgc aatggactcc
actgcctgct tgaagtcctt gctcctgact gtcagtcagt acaaagccgt gaagtcagag
g +70

Figure 28

Nucleotide Sequence of A 5' CIP2A Promoter Deletion Construct Fragment (SEQ ID NO: 8)

-123 accggatccg gaagcttctg agagcgaggg ggtggggccg aaaatcaaaa aaagcgcggc
gaaagctaaa ggccggcgca cgctgggcgg tggtggtccc taagccgggc cgcggccggt
gcaatggact ccactgcctg cttgaagtcc ttgctcctga ctgtcagtca gtacaaagcc
gtgaagtcag agg +70

Figure 29

Nucleotide Sequence of A 5' CIP2A Promoter Deletion Construct Fragment (SEQ ID NO: 9)

-95 ggggtggggc cgaaaatcaa aaaaagcgcg gcgaaagcta aaggccggcg cacgctgggc ggtggtggtc cctaagccgg gccgcggccg gtgcaatgga ctccactgcc tgcttgaagt ccttgctcct gactgtcagt cagtacaaag ccgtgaagtc agagg +70

Figure 30

Nucleotide Sequence of A CIP2A Promoter Fragment Containing Ets1 and Elk1 Binding Sites (SEQ ID NO: 42)

-139 ggacttccgg agcccgaccg gatccggaag cttctgagag cgagggggtg gggccgaaaa
tcaaaaaaag cgcggcgaaa gctaaaggcc ggcgcacgct gggcggtggt ggtccctaag
ccgg -16

Figure 31

Nucleotide Sequence of A CIP2A Promoter Fragment That Does Not Contain Ets1 and Elk1 Binding Sites (SEQ ID NO: 43)

-2379 aaactggaaa ttaaaagcgt gagccactgc tcctggcctc ctgctccttt tcttcccttt
ttgaggccta aaagtatgga ttggtgtttc tcaaattagg atatgcaagt atctctgatt
aaaaatgtca agacttatca cagctagaaa cgatccctct tactaaactt acaacatcaa
ttttggtgaa gatttttga gaaagacatt tgatattaat tacagaagag aatacaaaat
ttgtatgact gcttaagtca aaatccaaca aagatggca -2101

SIRNA TARGETING ETS1 AND ELK1 AND METHOD OF USING SAME IN THE INHIBITION OF CIP2A GENE IN CANCER TREATMENT

CROSS-REFERENCE TO RELATED APPLICATIONS

This application claims the benefit under 35 U.S.C. §119 (e) to U.S. Provisional Application Nos. 61/604,152 filed Feb. 28, 2012, and 61/722,386 filed Nov. 5, 2012, the content of which is incorporated by reference herein in its entirety.

FIELD OF THE INVENTION

The present invention generally relates to the field of studying the promoter activity of the CIP2A oncogene and binding of transcriptional factors to the CIP2A gene promoter in cancer pathogenesis. Specifically, the present invention provides the use of siRNA targeting against transcriptional factors Ets1 and Elk1 to reduce their binding to the CIP2A gene promoter so as to inhibit the CIP2A gene activity and thereby attenuate tumor development.

BACKGROUND OF THE INVENTION

Cancerous inhibitor of protein phosphatase 2A (CIP2A) is a 90 kDa auto-antigen reported to be expressed in hepatocellular carcinoma of cancer patients (Hoo et al. 2002). CIP2A is believed to be an oncoprotein, and has a diverse array of functions including the inhibition of protein phosphatase 2A (PP2A) via dephosphorylation of c-Myc. CIP2A is hypothesized to stabilize c-Myc activity, probably via the dephosphorylation of c-Myc at its amino acid 62 position of serine (S62) (Junttila and Westermarck, 2008). Li et al. and Côme et al. similarly disclose CIP2A's interaction with c-Myc. CIP2A may play a role in progression of cancers, including human cervical, gastric, and breast cancers (Junttila et al. 2007; Li et al. 2008; Côme et al. 2009).

Increased expression of CIP2A is reported in tissue samples from gastric, breast, oral, prostate, cervical, esophageal squamous cell, and non-small cell lung cancer, colon, ovarian and colorectal patients (Khanna et al. 2009; Katz et al. 2010; Vaarala et al. 2010; Liu et al. 2011; Qu et al. 2010; Dong et al. 2011). The increased expression of CIP2A in breast, non-small cell lung and early stage tongue cancer is found to be correlated with poor prognosis and therefore may serve as a biomarker for cancer disease progression (Khanna et al. 2008; Dong et al., 2011; Böckelman et al. 2011).

Considering the increased expression of CIP2A in various types of cancer and its putative role in cancer progression through inhibition of PP2A tumor suppressor activity, it is important to identify and characterize transcription factors that regulate CIP2A gene promoter and thus CIP2A gene regulation. However, scare information exists regarding CIP2A promoter regulation. Recently, Khanna et al. (2011) disclosed a role of a transcriptional factor (Ets1) in transcriptional regulation of CIP2A in human gastric and prostate cancer cells. These authors further speculated that Ets1 may act via the mitogen activated protein kinase signaling cascade. The exact role of Ets1 and other potential transcriptional factors requires confirmation. The transcriptional elements regulating the expression of CIP2A still remain unclear. Furthermore, whether the proposed transcriptional regulation may be applicable in other cancer cells is unknown.

There is a continuing need in understanding the transcriptional regulation of CIP2A and in identifying means to suppress the expression of CIP2A and attenuate cancer development. The present invention provides a novel approach to use siRNA to influence the CIP2A promoter activity and thus altering the cancer pathogenesis in human.

SUMMARY OF THE INVENTION

The present invention provides characterization the CIP2A promoter region and identification of specific transcription factors (i.e., Ets1 and Elk1) that regulate the CIP2A promoter. It is discovered that the CIP2A promoter regulation is cell type specific. Specifically, Ets1 and Elk1 are required to regulate CIP2A gene expression in cervical cancer cells as well as endometrial cancer cells.

The present invention provides a method of using siRNA approach targeting against the transcriptional factors to down regulate the CIP2A expression in human urogenital cancers including cervical and endometrial carcinoma cells. The present siRNA approach has practical utility in attenuating tumor oncogenes in women's diseases.

The present invention provides siRNAs as well as compositions of siRNA for inhibiting the expression of the CIP2A gene in a mammal. The present invention also provides compositions and methods for treating pathological conditions and diseases mediated by the expression of the CIP2A gene, such as in cervical or endometrial cancer. The siRNA of the present invention comprises an RNA strand (the anti-sense strand) having a region sufficient to hybridize to mRNA of CIP2A and causes CIP2A mRNA to degrade. Preferably, the siRNA is more than 15 nucleotides and less than 30 nucleotides in length, generally 20-25 nucleotides in length, and is substantially complementary to at least part of an mRNA transcript of the CIP2A gene.

In one aspect, the present invention provides a method of attenuating the gene expression of CIP2A, comprising the steps of: a) providing a first siRNA targeted against Ets1 transcriptional factor and a second siRNA targeted against Elk1 transcriptional factor; b) exposing the first siRNA and the second siRNA to a cell suspected of developing into tumor, wherein the first siRNA and the second siRNA attenuate the gene expression of CIP2A, thereby attenuating the tumor development of said cell.

In another aspect, the present invention provides a method for inhibiting CIP2A expression in a human, comprising the steps of administering to a human suspected of suffering from a cancer an effective amount of a first siRNA and a second siRNA, wherein the first siRNA targets against Ets1 and the second siRNA targets against Elk1. Preferably, the cancer is cervical cancer or endometrial cancer.

BRIEF DESCRIPTION OF THE DRAWINGS

FIG. 4 depicts the nucleotide sequence of the ~2.5 kb CIP2A promoter (SEQ ID NO: 1). The 2,448 bp CIP2A promoter fragment was obtained through PCR amplification from a genomic DNA using primers directed to amplify positions 7301-4854 on the GenBank Accession Number AC 092693.8 bearing the *Homo sapiens* 3q BAC clone RP11-161J9 complete sequence.

FIG. 5 depicts a schematic representation of a total of nine (9) CIP2A promoter luciferase (Luc) reporter constructs. Each of these reporter constructs contains a CIP2A promoter fragment (~2.5 kb to ~0.1 kb in length upstream of the CIP2A transcription start site (i.e., ATG)) that is fused to with the Luc reporter gene.

FIG. 10 also depicts the Ets1 and Elk1 binding sites control transcription of CIP2A in which six (6) different mutants were constructed. Mutated binding sites in the CIP2A promoter region are indicated in bold and are underlined. Deletions are indicated in bold, italics, and are underlined. CIP2A Mut1 targeted the binding sites for transcription factor NF-κB, CIP2A Mut2 targeted the binding site for transcription factor Ets1, CIP2A Mut3 was targeted towards the Elk1 binding site, and CIP2A Mut4 targeted the binding site for transcription factor Pax5, while CIP2A Mut5 and CIP2A Mut6 targeted the binding sites for Ets1 and Elk1.

FIG. 16A depicts the effects of Ets1 siRNA on Ets1 mRNA expression. HeLa cells were transiently transfected with 100 nM of Ets1 siRNA (SEQ ID NOs: 30, 31) or Ets1/Elk1 (SEQ ID NOs: 30, 31, 32, 33) or siRNA-scramble as the negative control. The siRNA transfected cells showed a decrease in Ets1 mRNA expression levels. FIG. 16B depicts the effect of Elk1 siRNA on Elk1 mRNA expression. HeLa cells were transiently transfected with 100 nM of Elk1 siRNA (SEQ ID NOs: 32, 33) or Ets1/Elk1 (SEQ ID NOs: 30, 31, 32, 33) or siRNA-scramble as the negative control. The siRNA transfected cells showed a decrease in Elk1 mRNA expression levels.

FIG. 22 depicts the nucleotide sequence of a CIP2A 5' deletion construct −1452/+70 (SEQ ID NO: 2).

FIG. 23 depicts the nucleotide sequence of a CIP2A 5' deletion construct −941/+70 (SEQ ID NO: 3).

FIG. 24 depicts the nucleotide sequence of a CIP2A 5' deletion construct −428/+70 (SEQ ID NO: 4.

FIG. 25 depicts the nucleotide sequence of a CIP2A 5' deletion construct −284/+70 (SEQ ID NO: 5).

FIG. 26 depicts the nucleotide sequence of a CIP2A 5' deletion construct −213/+70 (SEQ ID NO: 6).

FIG. 27 depicts the nucleotide sequence of a CIP2A 5' deletion construct −171/+70 (SEQ ID NO: 7).

FIG. 28 depicts the nucleotide sequence of a CIP2A 5' deletion construct −123/+70 (SEQ ID NO: 8).

FIG. 29 depicts the nucleotide sequence of a CIP2A 5' deletion construct −95/+70 (SEQ ID NO: 9).

FIG. 30 depicts the nucleotide sequence −16/−139 (SEQ ID NO: 42), within the CIP2A proximal promoter that has Est1 and Elk1 palindromic binding sites.

FIG. 31 depicts the nucleotide sequence −2101/−2379 (SEQ ID NO: 43), the distal region of the CIP2A promoter that does not have Ets1 and Elk1 palindromic binding sites.

DETAILED DESCRIPTION OF THE INVENTION

Figure 1:
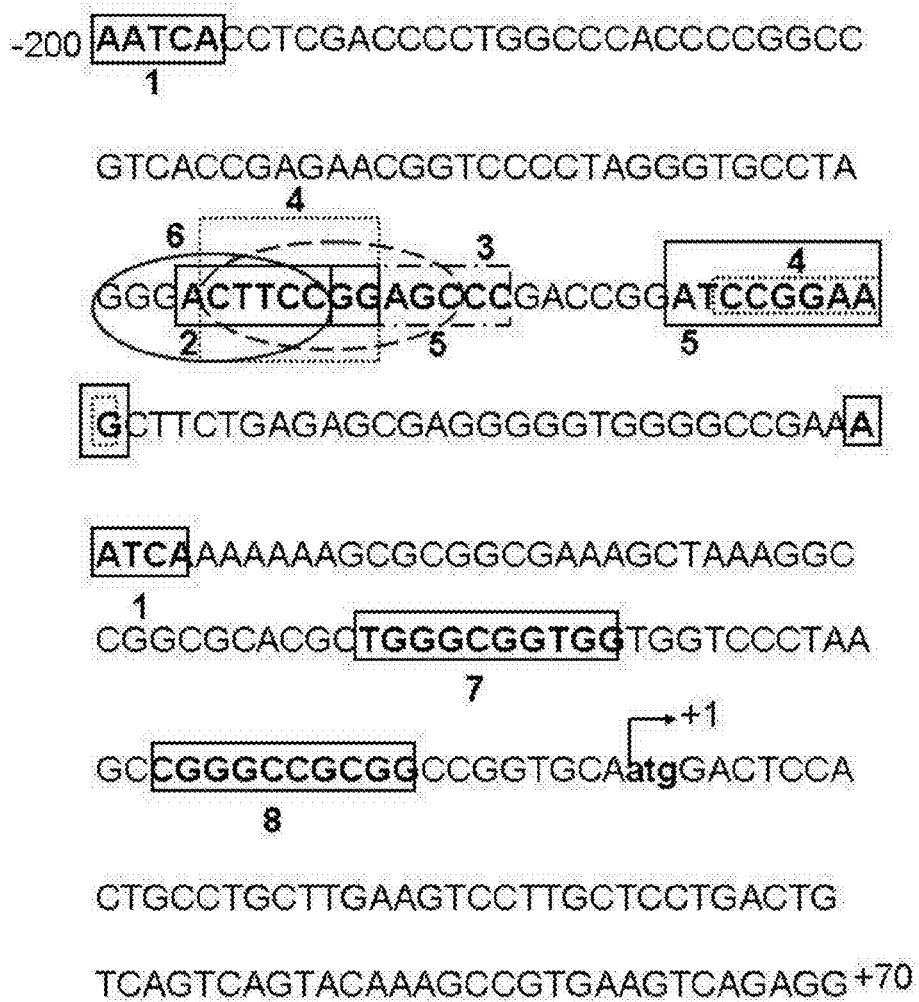
FIG. 1 depicts a schematic representation of putative transcription sites spanning the entire ~200 bp CIP2A promoter from the transcription start site (i.e., ATG). The putative transcription factor binding sites do not represent an exhaustive list and the transcription sites were identified using a bioinformatics program. The putative transcription factor binding sites have the following nucleotide sequences: 1) glucocorticoid receptor alpha: (AATCA) (nucleotides 2180-2184 of SEQ ID NO:1); 2) Retinoic acid receptor alpha: (ACTTCCGGAG) (nucleotides 2243-2252 of SEQ ID NO:1); 3) Pax5: (GGAGCCC) (nucleotides 2249-2255 of SEQ ID NO:1); 4) Ets1: (CTTCCGG) (nucleotides 2244-2250 of SEQ ID NO:1) or (CCGGAAG) (nucleotides 2264-2270 of SEQ ID NO:1); 5) Elk1: (CTTCCGGAG) (nucleotides 2244-2252 of SEQ ID NO:1) or (ATCCGGAAG) (nucleotides 2262-2270 of SEQ ID NO:1); 6) NF-κβ: (GGGACTTCC) (nucleotides 2240-2248 of SEQ ID NO:1); 7) Sp-1: (TGGGCGGTGG) (nucleotides 2340-2349 of SEQ ID NO:1); and 8) AP-2: (CGGGCCGCGG) (nucleotides 2361-2371 of SEQ ID NO:1).

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, the term "A," "T," "C", "G" and "U" refer to adenine, thymine, cytosine, guanine, uracil as a nucleotide base, respectively.

As used herein, the term "siRNA" refers to a small interfering RNA. RNA interference refers to the process of sequence-specific post-transcriptional gene silencing in a cell or an animal mediated by short interfering RNA.

As used herein, the term "siRNA targeted against Ets1" or "siRNA targeted against Elk1" refers to siRNA specifically promote degradation of Ets1 mRNA or Elk1 mRNA via sequence-specific complementary base pairings.

As used herein, the term "target sequence" refers to a contiguous portion of the nucleotide sequence of an mRNA molecule of a particular gene (i.e., CIP2A gene). The target sequence of a siRNA of the present invention refers to a mRNA sequence of that gene that is targeted by the siRNA by virtue of its complementarity of the anti-sense strand of the siRNA to such sequence and to which the anti-sense strand hybridizes when brought into contact with the mRNA. The mRNA sequence may include the number of nucleotides in the anti-sense strand as well as the number of nucleotides in a single-stranded overhang of the sense strand, if any.

As used herein, the term "complementary" refers to the ability of a first polynucleotide to hybridize with a second polynucleotide.

As used herein, the term "double-stranded RNA" ("dsRNA") refers to a complex of ribonucleic acid molecules having a duplex structure comprising two anti-parallel and substantially complementary nucleic acid strands.

As used herein, the term "nucleotide overhang" refers to the unpaired nucleotide or nucleotides that protrude from the duplex structure of a dsRNA when a 3'-end of one strand of the dsRNA extends beyond the 5'-end of the other strand, or vice versa.

As used herein, the term "palindromic" refers to a nucleotide sequence which is the same when read either in the 5'-3' direction or in the 3'-5' direction.

As used herein, the term "ectopic expression" refers to expression of a gene having a modified promoter when such a gene is being introduced into an organism for gene expression.

As used herein, the term "blunt" refers that there are no unpaired nucleotides at that end of the dsRNA (i.e., no nucleotide overhang). A "blunt ended" dsRNA is a dsRNA that has no nucleotide overhang at either end of the molecule.

As used herein, the term "anti-sense strand" refers to the strand of a dsRNA which includes a region that is substantially complementary to a target sequence.

As used herein, the term "sequence complementarity" refers to a sequence region on the anti-sense strand that is substantially complementary to a sequence. Where the sequence complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. Most preferably, the mismatches are located within 6, 5, 4, 3, or 2 nucleotides of the 5' terminus of the anti-sense strand and/or the 3' terminus of the sense strand.

As used herein, the term "sense strand," refers to the strand of a dsRNA that includes a region that is substantially complementary to a region of the anti-sense strand.

As used herein, the term "introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

As used herein, the terms "silencing" and "inhibiting the expression of", in as far as they refer to the CIP2A gene refers to at least partial suppression of the expression of the CIP2A gene, as manifested by a reduction of the amount of mRNA transcribed from the CIP2A gene. Alternatively, the degree of inhibition may be given in terms of a reduction of a parameter that is functionally linked to CIP2A gene transcription, e.g. the amount of protein encoded by the CIP2A gene which is secreted by a cell or found in solution after lysis of such cells.

As used herein, the term "CIP2A gene" refers to Cancerous Inhibitor Phosphate 2A gene, the nucleotide sequence of which is listed under Genbank accession numbers NM_020890.2, the disclosure of which is incorporated herein by reference.

As used herein, the term "deletion constructs" in the context of CIP2A promoter refers to the varying size fragments of the CIP2A promoter. The deletion constructions of CIP2A are obtained by sequentially deletion of the full-length CIP2A promoter by PCR and they are harbored in a pGL4 basic vector. The PCR is performing by maintaining the binding site of the reverser primer while altering the binding sites of a forward primer, thus creating CIP2A promoter fragments of varying sizes.

As used herein, the term "promoter" refers to a region of the DNA that facilitates the transcription of a particular gene.

As used herein, the term "~3 kb promoter fragment" refers to the −2379/+70 fragment of the CIP2A promoter and the nucleotide sequence of which is provided in FIG. 4.

As used herein, the term "Ets1" (E-twenty-six-specific) refers to a member of the family of transcription factors involved in regulating the expression of genes involved in apoptosis, development, differentiation, proliferation and transformation. The Ets family binds to the GGAA/T core motif and nucleotides flanking the core binding site increase specificity for Ets family member binding. The term "variant" refers to the different forms of the same protein (i.e., isoform) which differs in molecular weight and structure. For example, Ets1 variant 1 has a molecular weight of 55 kDa and represents the long isoform. The nucleotide sequence of the Ets1 mRNA variant 1 is listed under GenBank accession numbers NM_001143820.1, the disclosure of which is incorporated herein by reference. Ets1 variant 2 has a molecular weight of 51 kDa, and represents the short isoform. The nucleotide sequence of the Ets1 mRNA variant 2 is listed under GenBank accession numbers NM_005238.3, the disclosure of which is incorporated herein by reference.

As used herein, the term "Elk1" (Ets like kinase 1) refers to one of the Ets family member transcription factors known to regulate the expression of c-fos in cooperation with serum response elements (SRE). Elk1 shows preference for binding the consensus sequence CCGGAAGTR often with a second transcription factor SRE. Elk1 variant 1 and Elk1 variant 2 encode the same protein. However, Elk1 variant 2 differs from Elk1 variant 1 in that it lacks an internal 5'-UTR. The nucleotide sequence of the Elk1 mRNA variant 1 is listed under GenBank accession numbers NM_001114123.1, the disclosure of which is incorporated herein by reference. The nucleotide sequence of the Elk1 mRNA variant 2 is listed under GenBank accession numbers NM_005229.4, the disclosure of which is incorporated herein by reference.

As used herein, the term "pGL4" refers to the vector that encodes the luciferase reporter gene luc2 (*Photinus pyralis*) with high expression. The pGL4 vector is optimized for recombinant expression in mammalian cells. pGL4 basic has multiple cloning sites that allow the cloning of the promoter of interest.

As used herein, the term "luciferase activity" refers to the use of luciferase reporter to assess the transcriptional activity of a particular gene construct in a cell under the control of a promoter of interest.

As used herein, the term "cervical cancer" refers to the cancer that starts at the cervix (lower part of the uterus) and spreads to the top of the vagina.

As used herein, the term "endometrial cancer" refers to the cancer that starts at the endometrium, the tissue lining of the uterus. Endometrial cancer is also referred to as uterine cancer.

As used herein, the terms "attenuate", "treat" and "treatment" refer to relief from or alleviation of pathological processes mediated by CIP2A expression. In other words, relief from or alleviate at least one symptom associated with such condition, or to slow or reverse the progression of such condition.

The term "attenuate gene expression" refers to the use of siRNA molecule to down regulate the expression of target gene mRNA such as Ets1 or Elk1, which thereby leads to reduced expression of these genes.

As used herein, the term "quantitative PCR" refers to the quantitative polymerase chain reaction. Quantitative PCR is a means for quantifying the amount of template DNA present in the original mixture, usually achieved by the addition of a known amount of a target sequence that is amplified by the same primer set but can be differentiated, usually by size, at the end of the reaction.

As used herein, the term "real-time PCR" refers to the real-time polymerase chain reaction. Real-time PCR is a method for the detection and quantitation of an amplified PCR product based on a fluorescent reporter dye; the fluorescent signal increases in direct proportion to the amount of PCR product produced and is monitored at each cycle, 'in real time', such that the time point at which the first significant increase in the amount of PCR product correlates with the initial amount of target template.

As used herein, the term "pharmaceutical composition" comprises a pharmacologically effective amount of a dsRNA and a pharmaceutically acceptable carrier.

As used herein, the term "pharmaceutically acceptable carrier" refers to a carrier for administration of a therapeutic agent.

As used herein, the term "therapeutically effective amount" refers to an amount that provides a therapeutic benefit in the treatment, prevention, or management of pathological processes mediated by CIP2A expression or an overt symptom of pathological processes mediated by CIP2A expression.

In one aspect, the present invention provides characterization of the human CIP2A promoter including both the proximal and minimal proximal promoter. The present inventors show that the GGAA-binding transcription factors (e.g., Ets1 and Elk1) function together to regulate CIP2A gene expression in human cervical, endometrial and liver carcinoma cells. The 5' flanking minimal proximal promoter of the CIP2A gene consists of putative binding sites for Ets1 and Elk1 in forward and reverse orientations.

In another aspect, the present invention provides cloning of various human CIP2A promoters. In doing so, the present inventors identified two (2) Ets1/Elk1 binding sites in reverse orientations in the CIP2A promoter required for CIP2A gene expression. Without wishing to be bound by a theory, the presence of two (2) Ets1 binding sites is speculated that they may enhance the association between Ets/Ets homodimers by stabilizing the interaction and thus overcoming the auto-inhibitory domain of Ets transcription factors. It is an unexpected finding that both Ets1 and Elk1 (i.e., not just Ets1 alone or Elk1 alone) are required to regulate CIP2A. The presence of two (2) Ets1 binding sites still could not provide an explanation as to our surprising finding that both Ets1 and Elk1 are together required for regulating CIP2A gene expression in cells.

In another aspect, the present invention provides that Ets1 and Elk1 binding are essential for CIP2A basal expression in urogenital cancer cells, cervical cancer cells, endometrial cancer cells and liver carcinoma cells. siRNA knock-down of Ets1 and Elk1 together decrease CIP2A gene transcription, whereas knock-down of Ets1 or Elk1 alone does not decrease CIP2A gene transcription. Ectopic expression of Ets1 and Elk1 together increase CIP2A expression. There is a direct correlation between the levels of CIP2A and the levels of Ets1 and Elk1. The present findings indicate that the binding of Ets1 and Elk1 to the proximal CIP2A promoter is required for CIP2A expression in cancer cells.

In another aspect, the present invention provides the minimal promoter construct that provides gene regulation for CIP2A. In one embodiment, the present invention identifies and characterizes the transcriptional factors that control CIP2A expression. Utilizing functional deletion constructs of CIP2A gene, the present inventors discovered that the region between −123 and −95 of the CIP2A gene promoter is essential for the basal transcription in human cervical (HeLa), liver (HepG2), and endometrial carcinoma (ECC-1) cells. Transcriptional factors Ets1 and Elk1 are required for regulating the transcription of the CIP2A gene in human cervical and endometrial carcinoma cells.

The present invention therefore provides a therapeutic strategy of using siRNA targeted against Ets1 and Elk1 as a treatment for endometrial and cervical cancers. The present inventors provided the first elucidation for the transcriptional regulation of CIP2A in female urogenital cancers. The disclosed data find support in human CIP2A gene basal proximal and minimal proximal promoter in ECC-1 and HeLa cell lines. It is proposed that the GGAA binding transcription factors such as Ets1 and Elk1 work in a co-operative manner in the basal regulation of CIP2A expression in human cervical and endometrial carcinoma cells.

In one embodiment, the data support the minimal proximal promoter of CIP2A lies between −123/+70. Both Ets1 and Elk1 bind to this palindromic region to regulate the CIP2A expression. Without being bound by a theory, it is believed that the presence of palindromic Ets1 binding sites enhances an association between Ets1/Ets1 heterodimers by creating a stable interaction in the DNA binding domain, which overcomes the auto-inhibitory domain the Ets DNA binding region. The Ets-DNA binding is flanked by N- and C-terminal inhibitory regions that cause auto-inhibition and impair DNA binding.

In one embodiment, the present invention provides an observation that CIP2A luciferase activity was decreased when the Mut4 construct (Pax5 mutation) was expressed in ECC-1 cells when compared to the proximal promoter (−171/+70). However, expression was equal to the activity of the minimal proximal promoter region (−123/+70), which suggests that Pax5 may not be a major transcription factor regulating CIP2A in ECC-1 cells. This difference may be explained by a cooperative interaction between Pax5 and Elk1. It is speculated that the recruitment of Elk1 and Net by Pax5 may form a functional ternary complex in the B-cell specific promoter. Association with Pax5 may alter the Ets1 binding motif from GGAA to GGAG upon their interaction. It is surprising to note that it is possible that different regions of the CIP2A gene regulate basal transcription in different cell types.

In another embodiment, the present invention provides the observation that Ets1 binding is essential. Mutations in the Ets1 binding sites within the CIP2A gene promoter result in a decrease in the CIP2A promoter activity (e.g., in human gastric adenocarcinoma (AG 1478) cells).

In another embodiment, the present invention further provides an observation that there is a requirement for both Ets1 and Elk1 in CIP2A transcription in HeLa and ECC-1 cells (i.e., urogenital cancers). The present discovery is in sharp contrast to that of Khanna et al. (*PLOS* 2011, 6: 1-13) who suggested that Ets1 transcription factor alone regulates CIP2A expression levels in human gastric (AG1478) and prostate (PC-3 and LNCaP) carcinoma cells. Contrary to Khanna et al., the present discovery illustrates Ets1 and Elk1 are both required in cervical and endometrial cells, evidencing that there is cell-type specific regulation of CIP2A.

In one aspect, the present invention provides an isolated double stranded short interfering ribonucleic acid (siRNA) molecule that silences expression of Ets1 mRNA. In another aspect, the present invention provides an isolated double stranded short interfering ribonucleic acid (siRNA) molecule that silences expression of Elk1 mRNA.

The mechanism of action of siRNA is understood by one skilled in the art. Interfering RNA (RNAi) generally refers to a single-stranded RNA or double-stranded RNA (dsRNA). The dsRNA is capable of targeting specific messenger RNA (mRNA) and silencing (inhibiting) the expression of a target gene. During the process, dsRNA is enzymatically processed into short-interfering RNA (siRNA) duplexes of 21 nucleotides in length. The anti-sense strand of the siRNA duplex is then incorporated into a cytoplasmic complex of proteins (RNA-induced silencing complex or RISC). The RISC complex containing the anti-sense siRNA strand also binds mRNA which has a sequence complementary to the anti-sense strand—allowing complementary base-pairing between the anti-sense siRNA strand and the sense mRNA molecule. The mRNA molecule is then specifically cleaved by an enzyme (RNase) associated with RISC resulting in specific gene silencing. For gene silencing or knock down (i.e., mRNA cleavage) to occur, anti-sense RNA (i.e., siRNA) has to become incorporated into the RISC. This represents an efficient process that occurs in nucleated cells during regulation of gene expression. When an anti-sense DNA molecule is introduced into a cell, it targets specific mRNA through base-pairing of the anti-sense DNA molecule to its RNA target.

For purposes of this application, the anti-sense strand of the siRNA may comprise a contiguous nucleotide sequence, where the base sequence of the anti-sense strand has sequence complementarity to the base sequence of contiguous nucleotide sequence of corresponding length contained in the mRNA sequence of the targeted mRNA (e.g., Ets1 or Elk1 mRNA). Complementary includes complete base-pairing match or a few base-pairing mis-match.

In one embodiment, the anti-sense strand of the siRNA molecule comprises or consists of a sequence that is 100% complementary to the target sequence or a portion thereof. In another embodiment, the anti-sense strand of the siRNA molecule comprises or consists of a sequence that is at least about 90%, 95%, or 99% complementary to the target sequence or a portion thereof. For purposes of this application, the anti-sense strand of the siRNA molecule comprises or consists of a sequence that specifically hybridizes to the target sequence or a portion thereof so as to inhibit the target mRNA expression.

Without wishing to be bound by a theory, siRNA-mediated RNA interference may involve two-steps: (i) an initiation step, and (ii) an effector step. In the first step, input siRNA is processed into small fragments, such as 21-23-nucleotide 'guide sequences'. The guide RNAs can be incorporated into a protein-RNA complex which is capable of degrading mRNA, the nuclease complex, which has been called the RNA-induced silencing complex (RISC). The RISC complex acts in the second effector step to destroy mRNAs that are recognized by the guide RNAs through base-pairing interactions. siRNA involves the introduction by any means of double stranded RNA into the cell which triggers events that cause the degradation of a target RNA. siRNA is a form of post-transcriptional gene silencing. One of ordinary skill in the art would understand the preparation and utilization of siRNA molecules. (See, e.g., Hammond et al., *Nature Rev Gen* 2: 110-119 (2001); Sharp, *Genes Dev* 15: 485-490 (2001), the disclosure of which are incorporated herein by reference in their entireties).

Methods for preparing and isolating siRNA are known in the art (See, e.g., Smabrook et al., *Molecular Cloning, A Laboratory Manual* (2$^{nd}$ Ed., 1989), the disclosure of this is herein incorporated by reference in its entirety). In one embodiment, siRNA are chemically synthesized, using any of a variety of techniques known in the art, such as those described in Wincott et al., *Nucl. Acids Res.*, 23:2677-2684 (1995); and Wincott et al., *Methods Mol. Bio.*, 74:59 (1997). The synthesis of the siRNA makes use of common nucleic acid protecting and coupling groups, such as dimethoxytrityl at the 5'-end and phosphoramidites at the 3'-end. Suitable reagents for siRNA synthesis, methods for RNA deprotection, and methods for RNA purification are known to those of skill in the art. Small scale syntheses or large scale syntheses can be conducted using suitable synthesizer and protocols that are recognized in the industry. Preferably, siRNA molecules are chemically synthesized.

siRNA molecules can also be synthesized via a tandem synthesis technique, wherein both strands are synthesized as a single continuous strand separated by a cleavable linker that is subsequently cleaved to provide separate strands that hybridize to form the siRNA duplex. The tandem synthesis of siRNA can be readily adapted to both multi-well or multi-plate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the anti-sense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and anti-sense regions hybridize to form a siRNA duplex having hairpin secondary structure.

In one embodiment, siRNA comprises a double stranded region of about 15 to about 30 nucleotides in length. Preferably, siRNA has about 20-25 nucleotides in length. The siRNA molecules of the present invention are capable of silencing the expression of a target sequence in vitro and in vivo.

In one embodiment, the siRNA comprises a hairpin loop structure. In another embodiment, the siRNA has an overhang on its 3' or 5' ends relative to the target RNA which is to be cleaved. The overhang may be 2-10 nucleotides long. In one embodiment, the siRNA does not have an overhang (i.e., blunted).

In another embodiment, the siRNA molecule may contain one modified nucleotide. In yet another embodiment, the siRNA may comprise one, two, three four or more modified nucleotides in the double-stranded region. Exemplary modified siRNA molecule includes, but not limited to, modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and the like. The preparation of modified siRNA is known by one skilled in the art.

Because CIP2A overexpression has been proposed to correlate with the drug resistance in tumor treatment. Specifically, CIP2A is overexpressed in breast cancer cells and is correlated with the development of doxorubicin resistance (Choi et al., *FEBS Lett.* 2011; 585: 755-60). Another exemplary observation comes from the finding that overexpression of CIP2A in hepatocellular carcinoma cells (HCC) PLC5 leads to resistance to bortezomib (Chen et al., *Oncogene* 2010; 29: 6257-66). The present observation that there is a correlation in the CIP2A protein expression, Ets1 and Elk1 in six (6) matched pair of human cervical tumor samples further substantiates the important role of Ets1 and Elk1. The present invention provides a therapeutic approach of employing siR-NAs to block the Ets1 and Elk1 expressions and thus reduces the CIP2A expression and attenuate the tumor development.

In one aspect, the present invention provides two exemplary anti-sense strand siRNAs that hybridize to the Ets1 mRNA so as to increase degradation of Ets1 mRNA (and consequently Ets1 protein expression). In one embodiment, the present invention provides a first exemplary anti-sense strand siRNA (SEQ ID NO: 30) that hybridzises to Ets1 mRNA. This first exemplary anti-sense strand siRNA hybridizes to the Ets1 mRNA variant 1 (SEQ ID NO: 34) or Ets1 mRNA variant 2 (SEQ ID NO: 35).

In another embodiment, the present invention provides a second exemplary anti-sense strand siRNA (SEQ ID NO: 31) that hybridzises to Ets1 mRNA. This second exemplary anti-sense strand siRNA hybridizes to the Ets1 mRNA variant 1 (SEQ ID NO: 36) or Ets1 mRNA variant 2 (SEQ ID NO: 37).

In another aspect, the present invention also provides two exemplary an anti-sense strand siRNAs that hybridize to the Elk1 mRNA so as to increase degradation of Elk1 mRNA (and consequently Elk1 protein expression). In one embodiment, the present invention provides a first exemplary anti-sense strand siRNA (SEQ ID NO: 32) that hybridizes to Elk1 mRNA. This first exemplary anti-sense strand siRNA hybridizes to the Elk1 mRNA variant 1 (SEQ ID NO: 38) or Ets1 mRNA variant 2 (SEQ ID NO: 39).

In another embodiment, the present invention provides a second exemplary anti-sense strand siRNA (SEQ ID NO: 33) that hybridizes to Elk1 mRNA. This second exemplary anti-sense strand siRNA hybridizes to the Elk1 mRNA variant 1 (SEQ ID NO: 40) or Elk1 mRNA variant 2 (SEQ ID NO: 41).

In one embodiment, the present siRNA molecule targeting Ets1 is capable of silencing the Ets1 mRNA at least about 40%-100% of the expression of the target sequence relative to the corresponding unmodified (i.e., control) siRNA sequence. In another embodiment, the present siRNA molecule targeting Elk1 is capable of silencing the Elk1 mRNA at least about 40%-100% of the expression of the target sequence relative to the corresponding unmodified (i.e., control) siRNA sequence.

The present siRNA molecule targeting Ets1 and Elk1 can be used to down-regulate or inhibit the expression of CIP2A. The CIP2A expression is inhibited by at least about 40%-100%.

Our present finding is further supported by the ChIP study. The ChIP results support the hypothesis that both Elk1 and Est1 are associated with the CIP2A gene promoter in cervical cells (e.g., HeLa cells). Both Elk1 and Ets1 transcriptional factors are found to be associated with CIP2A gene promoter, albeit the Elk1 binding is stronger than that of Ets1 in associating with the CIP2A gene promoter. The present finding is entirely unexpected. To the best of the present inventors' knowledge, this represents the first reported observation that demonstrates that Elk1 can regulate CIP2A expression as well as the co-operative manner of both Elk1 and Ets1 in regulating CIP2A gene.

siRNA may conveniently be delivered to a target cell through a number of direct delivery systems. For example, siRNA may be delivered via electroporation, lipofection, calcium phosphate precipitation, plasmids, viral vectors, viral nucleic acids, phage nucleic acids, phages, cosmids, or via transfer of genetic material in cells or carriers such as cationic liposomes. In one embodiment, transfection of siRNA may employ viral vectors, chemical transfectants, or physico-mechanical methods such as electroporation and direct diffusion of DNA. The siRNA delivery methods are known in the art and readily adaptable for use. (See, e.g., Wolff, J. A., et al., Science, 247, 1465-1468, (1990); and Wolff, J. A. Nature, 352, 815-818, (1991)).

In one aspect, the present invention provides a pharmaceutical composition containing siRNAs targeted against Ets1 and Elk1 for the treatment of cervical cancer and endometrial cancer. The pharmaceutical composition comprises the siRNAs as therapeutic agents for inhibiting CIP2A gene activity and a pharmaceutical acceptable carrier. Pharmaceutically acceptable carriers include, but are not limited to, excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to aid absorption in the gastrointestinal tract.

In one embodiment, the present invention provides a kit containing anti-sense oligonucleotide against Elk1 and Ets1 as well as an instruction for use of such reagents in exposing cells in order to inhibit CIP2A gene expression in the cells. Alternatively, the instruction may include use of the present anti-sense oligonucleotide reagents in a mammal for the treatment of endometrial and cervical cancers.

In one embodiment, the present invention provides that the use of an anti-sense oligonucleotide against Elk1 and Ets1 that would lead to inhibiting CIP2A gene expression in order to suppress tumor development or growth. The present findings have practical utility for the therapeutic application of the anti-sense oligonucleotide against Elk1 and Ets1 through inhibition of CIP2A in cancer treatment. Specifically, the use of anti-sense Elk1 and Ets1 can be used as a therapeutic agent in treating cervical cancer and endometrial cancer. The present reagents may be used in combination with other routine anti-cancer drug therapy.

One aspect of the present invention relates to a method of anti-sense therapy, the method comprising the step of administering to a mammal in need thereof, an effective therapeutic (or prophylactic) amount of at least one anti-sense oligonucleotide as disclosed in this application. This method is particularly useful for preventing and/or treating cervical cancer or endometrial cancer.

The present invention provides a method of treating or alleviating cancer progression in a human female subject which comprises administering to the subject an amount of any of the aforementioned compositions comprising anti-sense oligonucleotides against Ets1 and Elk1 transcriptional factors so as to block CIP2A gene expression. One of ordinary skill in the art would be able to conveniently determine a therapeutically effective amount of the anti-sense oligonucleotides (i.e., the amount necessary so that the oligonucleotide performs its biological function without causing, into the host to which the composition is administered, overly negative effects). The exact amount of anti-sense oligonucleotide to be used may be conveniently optimized by a physician. The present composition to be administered may vary according to factors such as the oligonucleotide biological activity, the type of condition being treated, the mode of administration, as well as the other ingredients in the composition.

Various dosage forms of the present pharmaceutical compositions containing siRNA may be administered to a mammal in vivo to treat cancer. Preferably, the mammal is a human subject. In one embodiment, the pharmaceutical formulation includes a dosage suitable for oral administration. In another embodiment, the pharmaceutical formulation is designed to suit various means for siRNA administration. Exemplary means include uptake of naked siRNA, liposome fusion, intramuscular injection via a gene gun, endocytosis and the like. These administration means are well known in the art.

The present invention provides a means for attenuating (i.e., inhibiting) the CIP2A gene using siRNA targeting against Ets1 and Elk1. It is known that increased CIP2A may be associated with the development of drug resistance in various cancer cells. For example, doxorubicin resistance in breast cancer cells and bortezomib resistance in hepatocellular carcinoma cells. The present invention provides a method of reducing drug resistance in cancer cells by reducing Ets1 or Elk1 expression levels. Specifically, the present invention provides a method of using siRNA targeted against Ets1 and Elk1 in attenuating the CIP2A expression in urogenital cancers, including cervical cancer and endometrial cancer. The combined use of siRNA to attenuate Ets1 and Elk1 represents a prognostic tool in treating human cervical carcinoma.

In one embodiment, the siRNA is administered to a human with a therapeutic effective amount of siRNA targeting Ets1 or Elk1 transcriptional factors. The specific amount that is therapeutically effective can be readily determined by monitoring the CIP2A mRNA levels. Inhibition of Ets1 or Elk1 mRNAs is conveniently achieved by using qRT-PCR, Northern blot analysis and other techniques known to those of skill in the art such as dot blots, in situ hybridization, and the like. The inhibition level is comparing the target gene expression to the control. A detectable inhibition can be about 40%-100%. Preferably, the % inhibition may be 80%, 90% or 100%. The therapeutic effective amount may be determined by ordinary medical practitioner, and may vary depending on factors known in the art, such as the patient's history and age, the stage of pathological processes mediated by CIP2A expression.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

Cloning of CIP2A Promoters

CIP2A cDNA has been cloned by Hoo et al. (2002), and was identified as an auto-antigen over-expressed along with p62 in hepatocellular carcinoma patients sera. Thereafter, several authors recently reported increased expressions of CIP2A in various types of cancers cells and tumor samples from patients ranging from gastric, breast, oral, prostate, cervical, esophageal squamous cell carcinoma, non-small cell lung carcinoma, early-stage tongue cancer, acute myeloid leukemia, chronic myeloid leukemia and invasive rheumatoid arthritis (Li et al., 2008; Côme et al., 2009; Khanna et al., 2009; Katz et al., 2010; Vaarala et al., 2010; Liu et al., 2011; Qu et al., 2010; Dong et al., 2010; Lucas et al., 2011; Wang et al., 2011; Lee et al., 2011). However, the transcriptional elements regulating the expression of CIP2A in urogenital cancers have remained uncharacterized.

The CIP2A nucleotide gene sequence has been deposited in GenBank (GenBank accession no. AC092693.8), the disclosure of which is incorporated by reference. In this study, we specifically examined the genomic structure of the CIP2A promoter and the role of its transcriptional regulation. To do so, we prepared a CIP2A promoter construct upstream from that of the CIP2A transcription start site (i.e. ATG), and prepared 5'-deletion clones as well as the full-length 2.4 kilobasepairs (kbp) basal promoter clone. The first exon was found between +1 and +70 nucleotides (FIG. 1). The 5' flanking region upstream of the transcription start site (TSS)+1 region is predicted to harbor the promoter region for transcriptional regulation of CIP2A.

We used PCR approach with a specific primer pair (SEQ ID NOs: 10 and 11) (See, Table 3) designed to amplify nucleotide positions 7301-4854 of the CIP2A gene with the GenBank Accession Number AC 092693.8 bearing the BAC clone RP11-161J9. The resulting PCR CIP2A cloned fragment has a nucleotide sequence listed in SEQ ID NO: 1 (See, Table 3 and FIG. 4).

Figure 2:
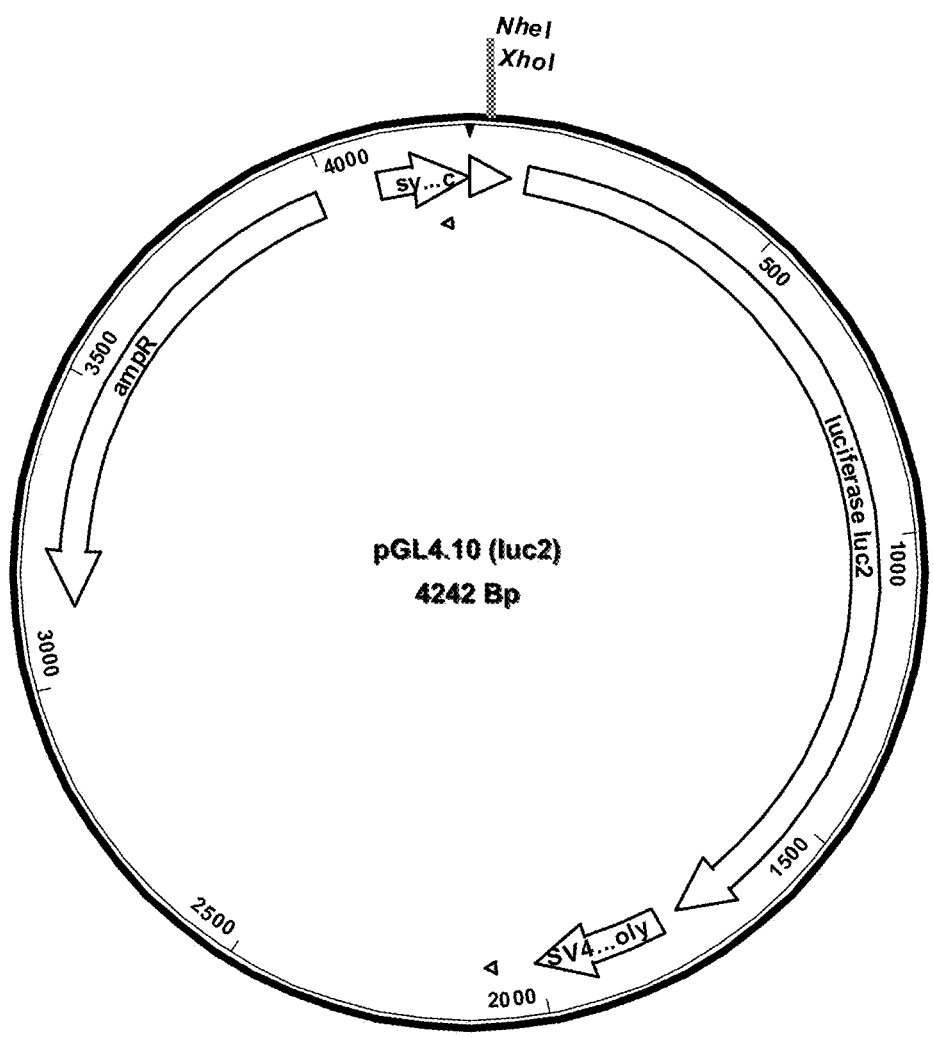
FIG. 2 depicts a schematic representation of the pGL4.10 [luc2] plasmid. This plasmid is 4,242 bp in length and contains the luciferase reporter gene and multiple cloning sites upstream of the luc gene. Additional features of the pGL4.10 [luc2] plasmid are indicated, including the NheI and XhoI restriction sites.
Figure 3:
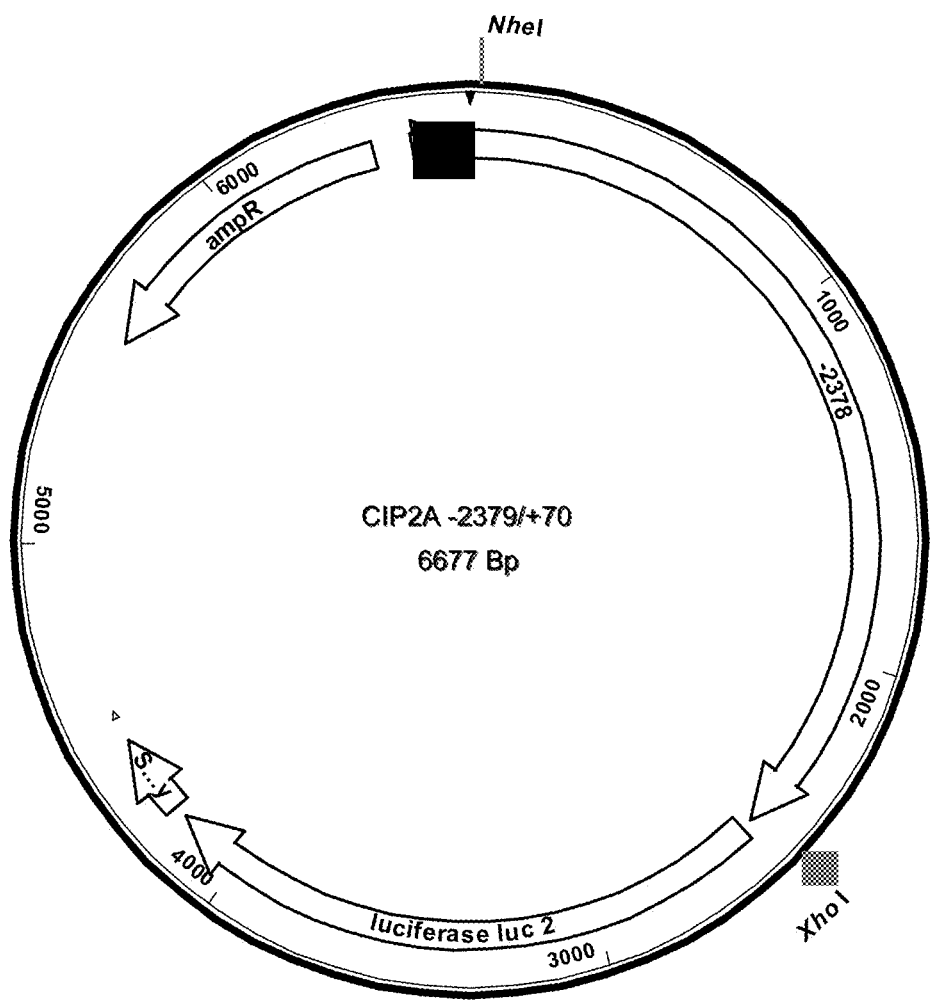
FIG. 3 depicts a schematic representation of the pGL4.10 [luc2] plasmid containing the CIP2A promoter. This plasmid is 6,677 bp in length and contains 2,379 bp upstream of the CIP2A coding gene region. Additional features of the CIP2A −2379/+70 are indicated, including the NheI and XhoI restriction sites.

The cloned DNA consisted of a promoter fragment containing ~3 kb that is upstream of the CIP2A transcription start site (i.e., ATG). The amplified ~3 kb promoter fragment was purified using gel extraction protocol. We then used restriction enzymes to insert the amplified ~3 kb promoter fragment into the luciferase reporter construct (i.e., pGL4.10 [luc2] luciferase reporter which contains only the luciferase coding region and no regulatory element) (See, FIG. 2). The resulting luciferase reporter construct containing the ~3 kb CIP2A promoter fragment is named CIP2A −2379/+70 plasmid (See, FIG. 3).

Example 2

Nucleotide Sequence of the ~3 kb CIP2A Promoter Fragments

The ~3 kb promoter fragment was sequence-verified. We used the SEQ ID NOs: 10 and 11 (Table 3) against the forward and reverse strands and the sequencing was performed on a CEQ 8000 Genomic analyzer (Beckman Coultier). We compared the sequence of the ~3 kb promoter fragment (SEQ ID NO: 1) with the nucleotide sequence of the CIP2A gene (GenBank Accession Number, AC 092693.8) and verified that there was no mutation introduced through PCR cloning. The nucleotide sequence (SEQ ID NO: 1) of our ~3 kb promoter fragment is listed in FIG. 4.

Example 3

Additional CIP2A Promoter Constructs (~1.4 kb, ~1 kb, ~0.5 kb, ~0.2 kb and ~0.1 kb)

So far, we have successfully cloned the ~3 kb CIP2A promoter in the luciferase reporter vector. In this study, we sought to identify the minimal proximal promoter region from CIP2A transcription start site (i.e., ATG) required for constitutive expression of CIP2A. We also identified the respective role of the putative transcriptional sites present on this CIP2A promoter region. To do so, we took the initiative to generate eight (8) additional CIP2A promoter constructs (in addition to the ~3 kb CIP2A promoter construct).

We cloned a total of nine (9) CIP2A promoter luciferase reporter constructs with various CIP2A promoter lengths from ~2.4 kb to ~0.1 kb. As described in Example 2, we used forward primer (SEQ ID NO: 10) and reverse primer (SEQ ID NO: 11) to clone out CIP2A −2379/+70 CIP2A clone. We utilized the CIP2A −2379/+70 construct (SEQ ID NO: 1) as the template for generating the various CIP2A promoter fragments. All the CIP2A promoter fragments were generated. The CIP2A clones included CIP2A −1452/+70 construct (SEQ ID NO: 2), CIP2A −941/+70 construct (SEQ ID NO: 3), CIP2A −428/+70 construct (SEQ ID NO: 4), CIP2A −284/+70 construct (SEQ ID NO: 5), CIP2A −213/+70 construct (SEQ ID NO: 6), CIP2A −171/+70 construct (SEQ ID NO: 7), CIP2A −123/+70 construct (SEQ ID NO: 8), and CIP2A −95/+70 construct (SEQ ID NO: 9).

Table 3 summarizes the forward primers and reverse primers used in generating various CIP2A clones. The forward primer and reverse primers used in preparing CIP2A −1452/+70 (SEQ ID NO: 2) were SEQ ID NOs: 12 and 13 respectively. The forward primer and reverse primers used in preparing CIP2A −941/+70 (SEQ ID NO: 3) were SEQ ID NOs: 14 and 15 respectively. The forward primer and reverse primers used in preparing CIP2A −428/+70 (SEQ ID NO: 4) were SEQ ID NOs: 16 and 17 respectively. The forward primer and reverse primers used in preparing CIP2A −284/+70 (SEQ ID NO: 5) were SEQ ID NOs: 18 and 19 respectively. The forward primer and reverse primers used in preparing CIP2A −213/+70 (SEQ ID NO: 6) were SEQ ID NOs: 20 and 21 respectively. The forward primer and reverse primers used in preparing CIP2A −171/+70 (SEQ ID NO: 7) were SEQ ID NOs: 22 and 23 respectively. The forward primer and reverse primers used in preparing CIP2A −123/+70 (SEQ ID NO: 8) were SEQ ID NOs: 24 and 25 respectively. The forward primer and reverse primers used in preparing CIP2A −95/+70 (SEQ ID NO: 9) were SEQ ID NOs: 26 and 27 respectively. All of the nine (9) CIP2A clones and their primer pairs are listed in Table 3. The primers utilized for PCR amplification consisted of NheI and XhoI restriction enzymes in the forward and reverser primers for cloning into the luciferase reporter vector. The sequences of all the nine (9) CIP2A constructs were verified by sequencing.

FIG. 5 summarizes the prepared luciferase reporter constructs harboring various CIP2A promoter fragments. Table 3 summarizes the prepared additional CIP2A promoter luciferase constructs that include 1.4 kb, ~1 kb, ~0.5 kb, ~0.2 kb and ~0.1 kb CIP2A promoter (upstream from transcription start site). The nucleotide sequence of these CIP2A promoter constructs is included in FIG. 4. The clone names of the various CIP2A constructs are also indicated.

Example 4

Identification of CIP2A Proximal and Minimal Proximal Promoter Regions

Figure 6:
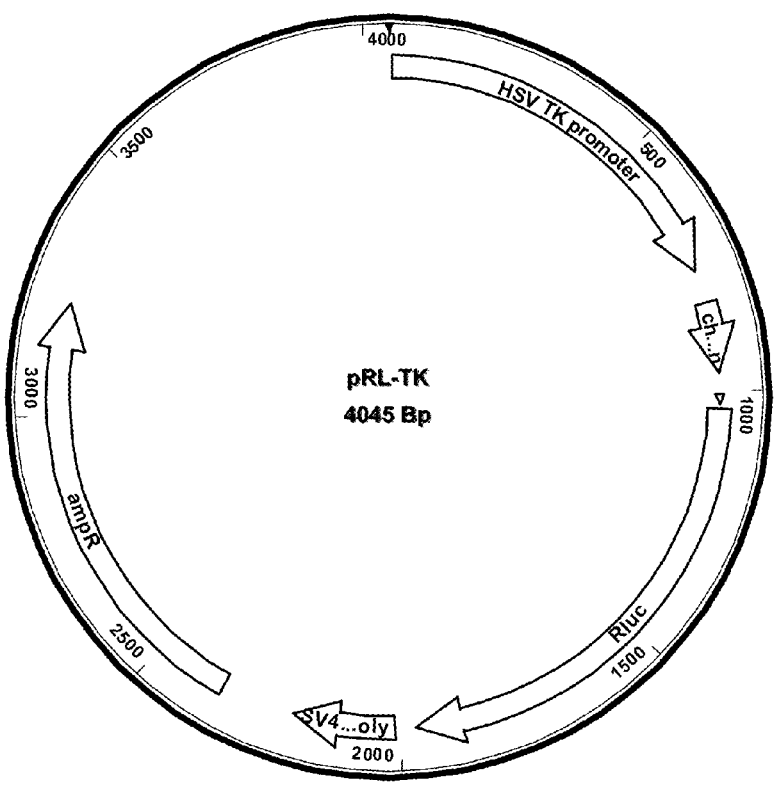
FIG. 6 depicts a schematic representation of the pRL-TK plasmid. This plasmid is 4,045 bp in length and contains the luciferase reporter gene *Renilla* and multiple cloning sites upstream of the Rluc gene. The pRL-TK plasmid consists of HSV TK promoter is used for optimization of transfection efficiency in luciferase assay.

In order to identify functional transcription factor binding sites in the 5' flanking region of the CIP2A gene promoter, we prepared a series of PCR deletion clones for CIP2A promoter using the pGL4 basic luciferase vector. FIG. 5 shows the constructed luciferase reporter constructs carried various CIP2A promoter fragments, with the pGL4 luciferase vector. In order to identify the CIP2A promoter region responsible for constitutive expression of CIP2A, we transiently transfected all the 5' CIP2A deletion constructs into either human cervical carcinoma cells (HeLa cells) or human liver hepatoblastoma cells (HepG2 cells). Moreover the cells were also transiently transfected with pRL-TK vector (FIG. 6) carrying the Renilla luciferase (RL) under with thymidine kinase (TK) promoter and enhancer elements for normalization of transfection efficiency. The fold change in relative luciferase activity (RLA) of individual deletion clone was compared with that of pGL4 basic vector (i.e., pGL4.10 [luc2] luciferase reporter which contains only the luciferase coding region and no regulatory element), which serves as the negative control.

(i) Human Cervical Carcinoma and Liver Hepatoblastoma

Figure 7:
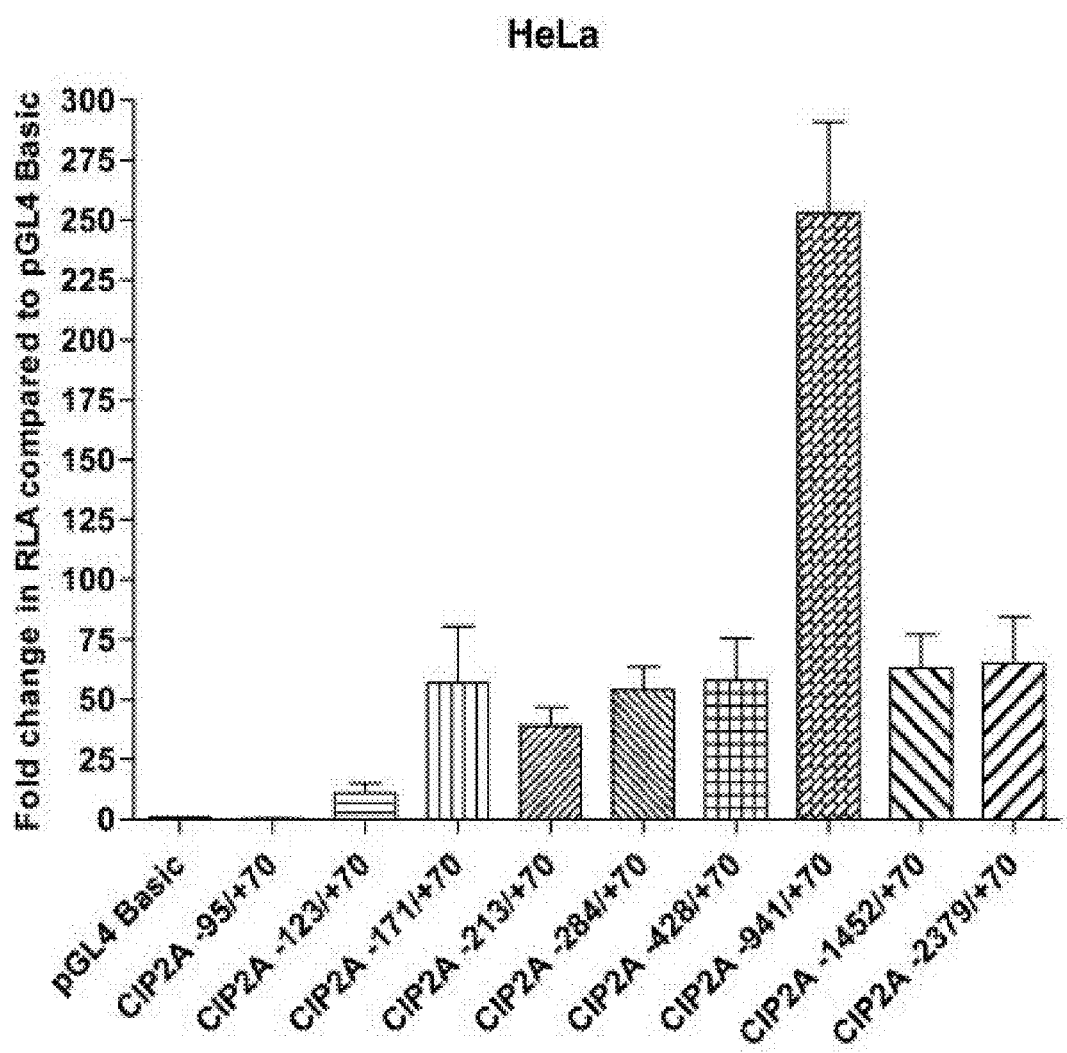
FIG. 7 depicts a luciferase assay in human cervical carcinoma cells (HeLa), which were transfected with various CIP2A promoter constructs as shown in FIG. 4 and assayed for luciferase activity after 48 hours. Fold increase in relative luciferase activity (RLA) was compared with pGL4 basic (value is set at 1). Normalization in transfection efficiency was performed by co-transfection with pRL-TK (*Renilla* expression vector). The means±S.D. are from three different experiments, each performed in triplicate.
Figure 8:
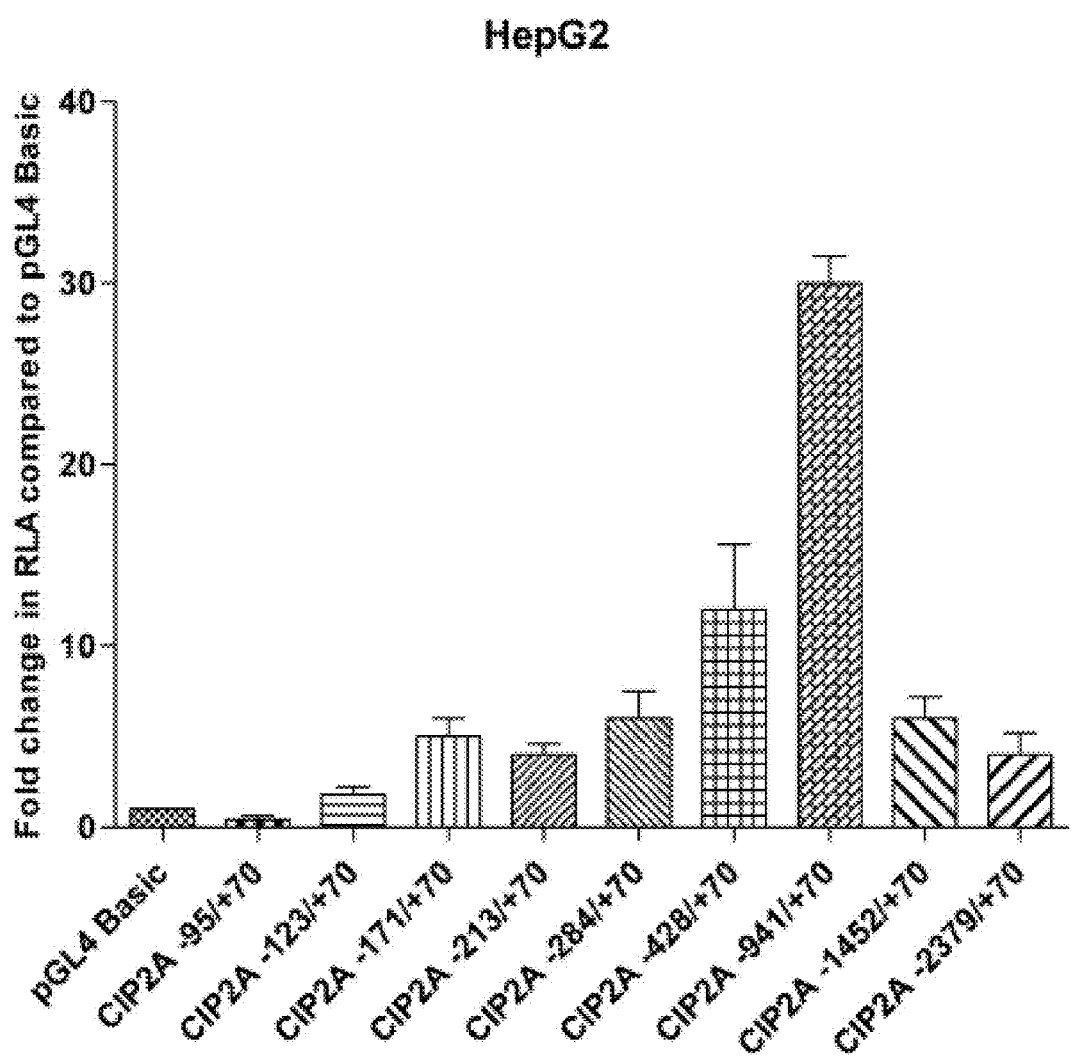
FIG. 8 depicts a luciferase assay in human liver carcinoma cells (HepG2), which were transfected with various CIP2A promoter constructs shown in FIG. 4 and assayed for luciferase activity after 48 hours. Fold increase in relative luciferase activity (RLA) was compared with pGL4 basic (set as 1). Normalization in transfection efficiency was performed by co-transfection with pRL-TK (*Renilla* expression vector). The means±S.D. are from three different experiments, each performed in triplicate.

We found that the full-length CIP2A promoter (−2379/+70) possessed a 50-fold increase in HeLa cells (FIG. 7) and a 5-fold increase in HepG2 cells (FIG. 8) when compared to the basic vector. The CIP2A −95/+70 clone showed no activity above background in these cells (FIGS. 7 and 8). The activity of promoter construct −171/+70 was similar to the full-length construct −2379/+70 of the CIP2A gene promoter. Based on the deletion constructs (FIG. 5), the construct containing the region −171/+70 displayed a 57- and 5-fold increase in RLA, while the promoter region −123/+70 showed 11- and 2-fold increase in RLA in HeLa and HepG2 cells when compared to pGL4 basic vector. These data indicate that clone −123/+70 contains the minimal proximal promoter activity of the human CIP2A gene.

We observed that the DNA fragment −941/+70 showed the highest (253- and 20-fold) increase in relative luciferase activity (RLA) in these cells (FIGS. 7 and 8). These data suggest there may be enhancer and/or corepressor binding sites upstream of the minimal proximal promoter, which further regulate the basic CIP2A activity mediated by the −123/+70 region.

In sum, these results indicate that the clone −123/+70 contain the minimal proximal promoter of the human CIP2A gene. Clones CIP2A −213/+70, CIP2A −284/+70, CIP2A −428/+70 and CIP2A −1452/+70 showed similar luciferase activity as that of CIP2A −171/+70 in HeLa and HepG2 cells (FIGS. 7 and 8).

(ii) Human Endometrial Carcinoma Cells

In a separate series of study, we assessed the CIP2A gene transcription in human endometrial (ECC-1) carcinoma cells. Deletion constructs harboring the promoter regions −123/+70, −171/+70, −428/+70, −941/+70 and −2379/+70 (FIG. 5) were utilized.

Figure 9:
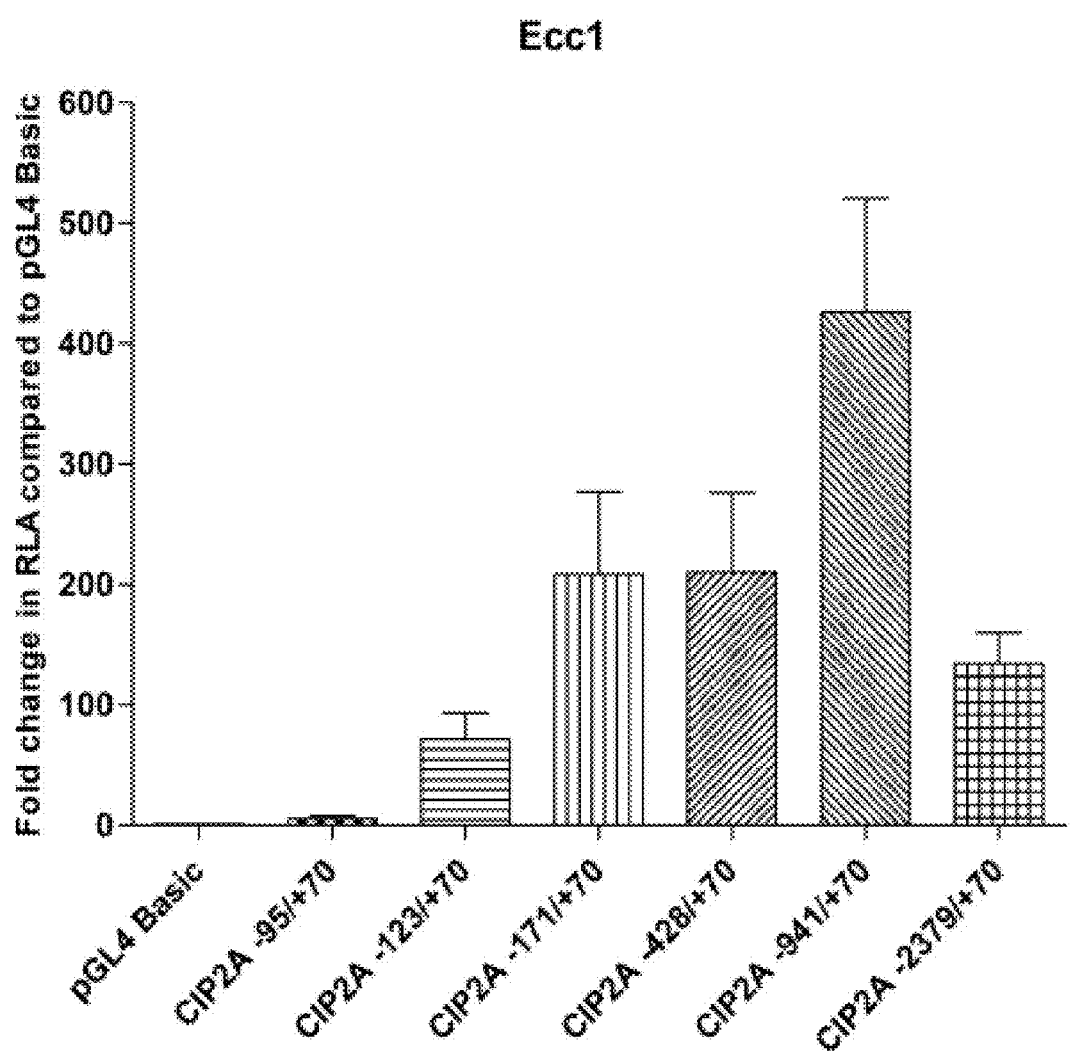
FIG. 9 depicts a luciferase assay in human endometrial carcinoma cells (ECC-1), which were transfected with various CIP2A promoter constructs as shown in FIG. 4 and assayed for luciferase activity after 48 hours. Fold increase in relative luciferase activity (RLA) was compared with pGL4 basic (set as 1). Normalization in transfection efficiency was performed by co-transfection with pRL-TK (*Renilla* expression vector). The means±S.D. are from three different experiments, each performed in triplicate.

A 71- and 283-fold increase in RLA was observed with CIP2A −123/+70, CIP2A −171/+70 clones in comparison with CIP2A −95/+70 clone which displayed only a 5-fold increase in RLA when compared to pGL4 Basic (FIG. 9). As was observed in HeLa and HepG2 cells, the CIP2A −941/+70 construct showed the highest activity, while the luciferase activity of MI-length construct −2379/+70 was similar to CIP2A −171/+70.

Altogether, these results identify the region between −123 to −95 as the minimal proximal promoter region. Such region is believed to be essential for regulating the transcription of human CIP2A gene promoter in human cervical, liver and endometrial carcinoma cells. The minimal proximal region corresponds with the nucleotide 5046-5018 of the BAC clone RP11-161J9 with CIP2A gene and GenBank Accession No. AC 092693.8. While the region between −123 and −95 constitutes the minimal proximal promoter essential for CIP2A expression in human cervical, liver and endometrial carcinoma cells, the region between −171 and −95 contains the proximal promoter. The data are summarized in Table 2.

Example 5

The ~200 bp CIP2A Proximal Promoter Contains Multiple Putative Transcription Factor(s) Binding Sites The CIP2A promoter is speculated to regulate through binding of transcription factors to the transcriptional sites present on the proximal promoter region. We next sought to identify putative transcription factor(s) binding sites present within the ~200 bp CIP2A proximal promoter. To do this, we performed a bioinformatics analysis of the ~200 bp human CIP2A promoter construct in order to indentify putative transcription factor(s) binding sites in this fragment. Specifically, we analyzed the proximal promoter region (−171 to −95) of the human CIP2A promoter for potential transcription factor binding sites.

We utilized two (2) bioinformatics programs: (i) ALIBABA 2.0 (www.gene-regulation.com) and (ii) ALGENPROMO (www.alggen.lsi.upc.es/cgi-bin/promo_v3/promo). With these programs, we predicted eight (8) potential transcription factor(s) binding sites. Binding sites for GRα (glucocorticoid receptor alpha), RARα (retinoic acid alpha), Pax5, Ets1, Elk1, AP-2 and Sp1 were identified within the −171 to +1 region (See, FIG. 1). FIG. 1 depicts the overlapping shared transcription factor(s) binding sites present on the ~200 bp human CIP2A promoter. The binding sites for the Ets-1 and Elk1 transcription factors were identified in reverse orientations in region between −110/−118 and −127/−137 (FIG. 1).

Example 6

Figure 10:
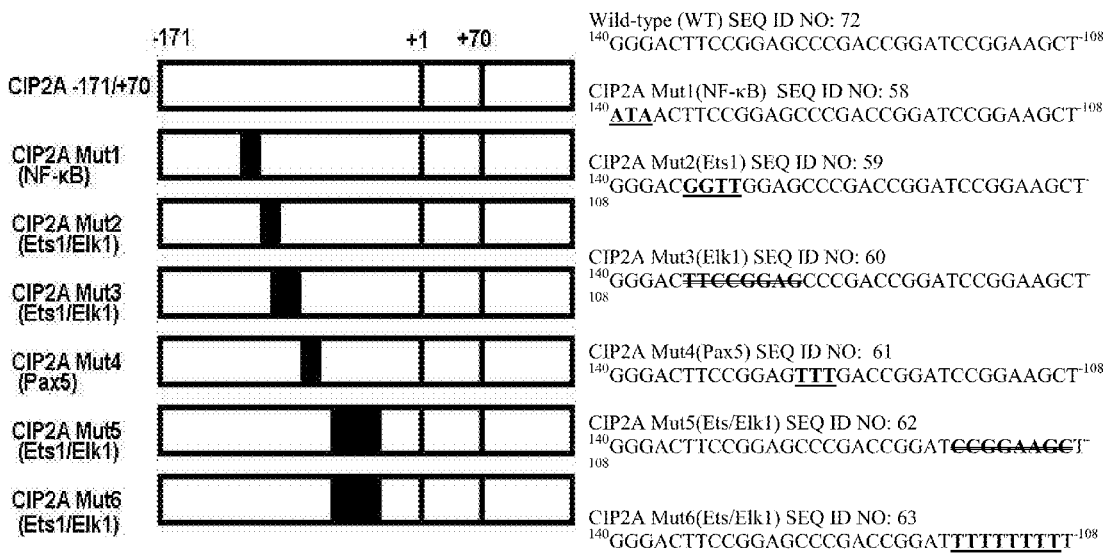
FIG. 10 depicts a schematic representation of six different mutants obtained utilizing site-directed mutagenesis. Transcription factor binding sites mutated in the CIP2A promoter region are indicated in bold, double-strike and are underlined. CIP2A Mut1 targeted the binding sites for transcription factor NF-κB, CIP2A Mut2 targeted the binding site for transcription factor Ets1, CIP2A Mut3 was targeted towards the Elk1 binding site, and CIP2A Mut4 targeted the binding site for transcription factor Pax-5, while CIP2A Mut 5 and CIP2A Mut 6 targeted the binding sites for Ets1/Elk1.

Deciphering the Specific Transcription Factor Important for Regulating the Transcription of CIP2A Promoter: Site-Directed Mutagenesis Studies Based on our results from the 5' deletion analysis and computational screening, we identified potential binding sites for NF-κB, RARα, Ets1, Elk1 and Pax5 transcription factor(s) in the region between −171 and −95 of the CIP2A gene promoter (the basal proximal promoter region). We next utilized PCR based site-directed mutagenesis, point mutations (bases highlighted in bold and underlined) or deletions (bases highlighted in bold with double strike) were introduced within the transcription factor binding sites (FIG. 10). The CIP2A −171/+70 construct was used in all the mutagenesis studies (FIG. 10).

We have constructed several human CIP2A promoter constructs having specific mutant promoter sites. In a first mutant CIP2A promoter construct, the transcription factor binding site for NF-κB in CIP2A −171/+70 construct was mutated (point mutations) to generate the mutant CIP2A Mut1 (SEQ ID NO: 58). In a second mutant CIP2A promoter construct, the first binding site for Ets1 was altered to generate the mutant CIP2A Mut2 (SEQ ID NO: 59). In a third mutant CIP2A promoter construct, the first binding site for Elk1 was deleted to generate the mutant CIP2A Mut3 (SEQ ID NO: 60). In a fourth mutant CIP2A promoter construct, the binding site for Pax5 was altered with base substitution to yield the mutant CIP2A Mut4 (SEQ ID NO: 61). In a fifth mutant CIP2A promoter construct, the second Ets1 binding site in CIP2A promoter region between −110 to −118 was deleted to generate the mutant CIP2A Mut5 (SEQ ID NO: 62). In a sixth mutant CIP2A promoter construct, the second Elk1 binding site in CIP2A promoter region was substituted to yield the mutant CIP2A Mut6 (SEQ ID NO: 63). (See, FIG. 10).

Figure 11:
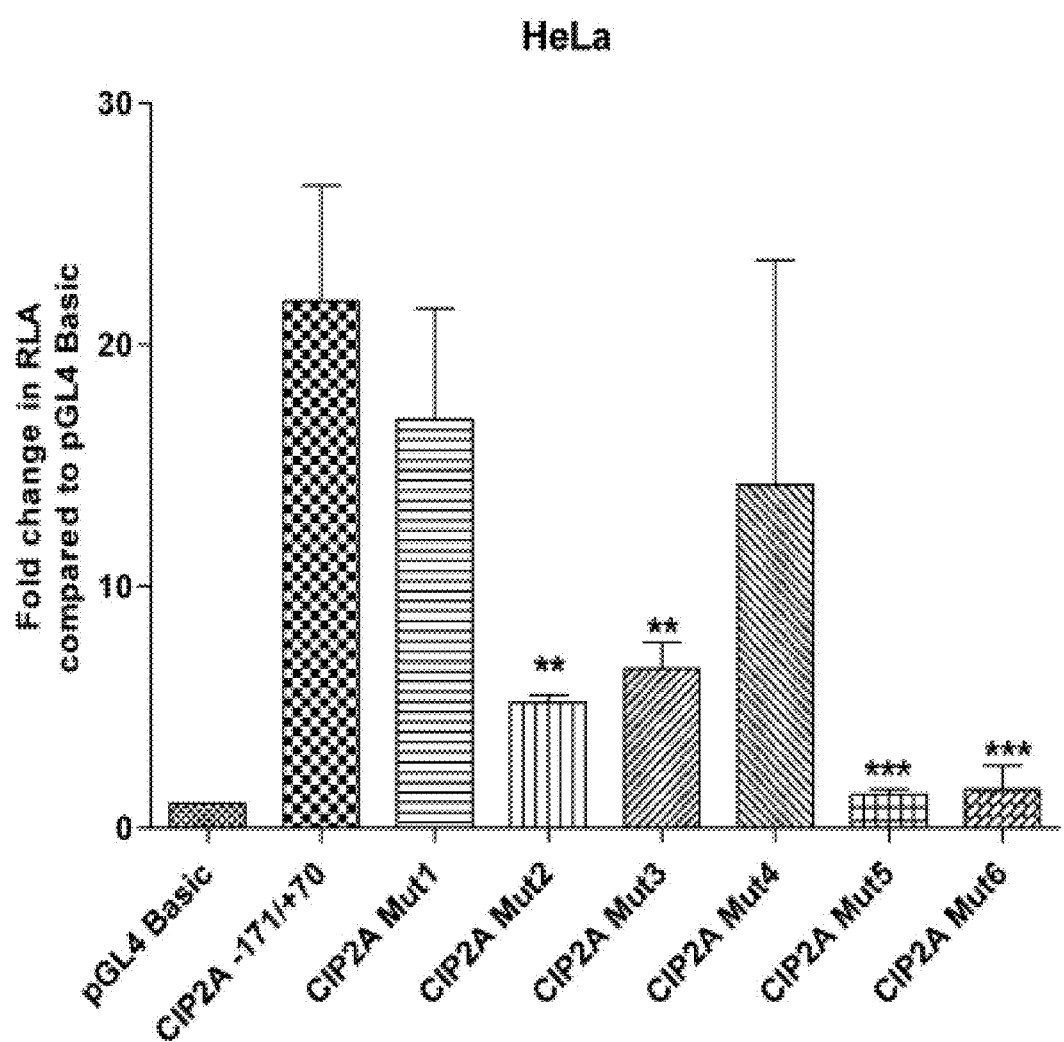
FIG. 11 depicts a luciferase assay in human cervical carcinoma (HeLa) transfected with Mut1, Mut2, Mut3, Mut4, Mut5 and Mut6 or the wild-type promoter (CIP2A −171/+70) and assayed for luciferase activity after 48 hours. Transfection efficiency was normalized by co-transfection with pRL-TK (*Renilla* expression vector). The means±S.D. are from three different experiments, each experiment performed in triplicate (*p>0.001, p>0.01, *p>0.05 with CIP2A −171/+70 compared to the control pGL4 basic vector and Mutant compared to CIP2A −171/+70 wild-type construct).
Figure 12:
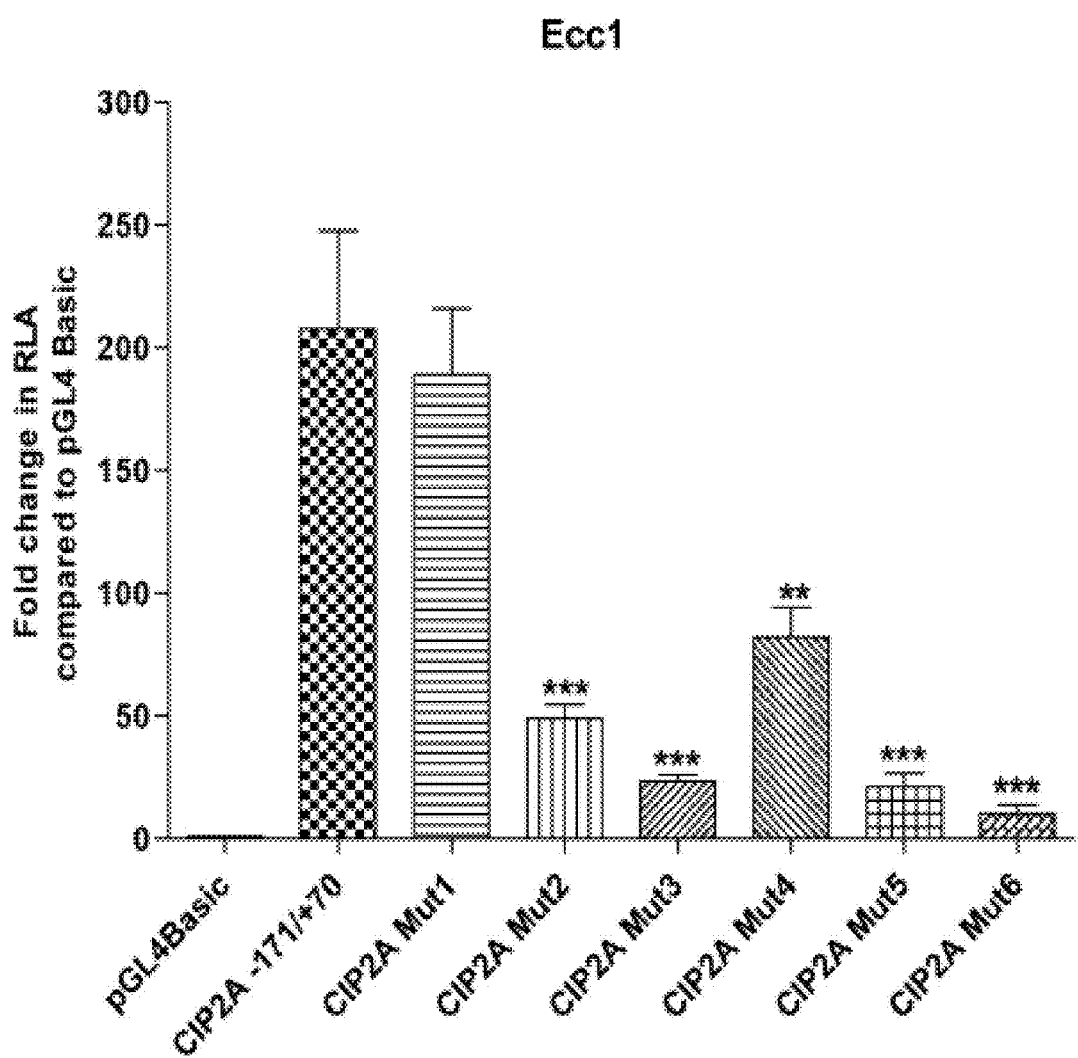
FIG. 12 depicts a luciferase assay in human endometrial carcinoma (ECC-1) transfected with Mut1, Mut2, Mut3, Mut4, Mut5 and Mut6 or the wild-type promoter (CIP2A −171/+70) and assayed for luciferase activity after 48 hours. Transfection efficiency was normalized by co-transfection with pRL-TK (*Renilla* expression vector). The means±S.D. are from three different experiments, each experiment performed in triplicate (*p>0.001, p>0.01, *p>0.05 with CIP2A −171/+70 compared to the control pGL4 basic vector and Mutant compared to CIP2A −171/+70 wild-type construct).

Transfection of the CIP2A Mut2 and CIP2A Mut3 construct displayed a 3-4 fold reduced activity in the HeLa cells and a 7-16 fold reduction in activity in the ECC-1 cells compared to the wild-type CIP2A −171/+70 construct (FIGS. 11 and 12). In contrast, the mutation in the NF-κB binding site (CIP2A Mut1 construct) did not affect the basal luciferase activity in the HeLa and ECC-1 cells compared to the wild type construct CIP2A −171/+70 (FIGS. 11 and 12).

Mutation in the Pax5 binding site (CIP2A Mut4) did not affect the transcription of the CIP2A gene promoter in the HeLa cells (FIG. 11), but decreased the CIP2A transcription by 2.5-fold in ECC-1 cells (FIG. 12), indicating cell-type specificity.

Moreover, when the HeLa and ECC-1 cells were transfected with CIP2A Mut5, a 9-16 fold loss in CIP2A promoter activity was observed. Similarly, the CIP2A Mut6 displayed a 13-39-fold decrease in luciferase activity compared to the wild-type construct CIP2A −171/+70 in HeLa and ECC-1 cells (FIGS. 11 and 12).

Altogether, these results suggest that the transcription factor binding sites for Ets1 and Elk1 are crucial for the basal, constitutive transcription of CIP2A gene in human cervical and endometrial cancer cells.

Example 7

In Vitro Binding of Ets1 and Elk1 Transcriptional Proteins to CIP2A Minimal Proximal Promoter Region Our data showed a requirement for Ets1 and Elk1 proteins in driving CIP2A gene transcription. In this study, we performed an Electrophoretic Mobility Shift Assay (EMSA) to examine the binding of Ets1 and Elk1 transcriptional factors to the CIP2A promoter region. EMSA, also commonly known as mobility shift electrophoresis or gel shift assay, represents an affinity electrophoresis technique that is used to study protein-DNA interactions. We used EMSA to determine if the Ets1 and Elk1 proteins bind to CIP2A minimal promoter constructs.

In this study, we first synthesized a wild-type (WT) probe harboring the Ets1 and Elk1 binding sites in the forward and reverse orientation from −138 to −107 bp of the CIP2A gene promoter with a consensus oligonucleotide for Ets1 and Elk1.

Figure 13:
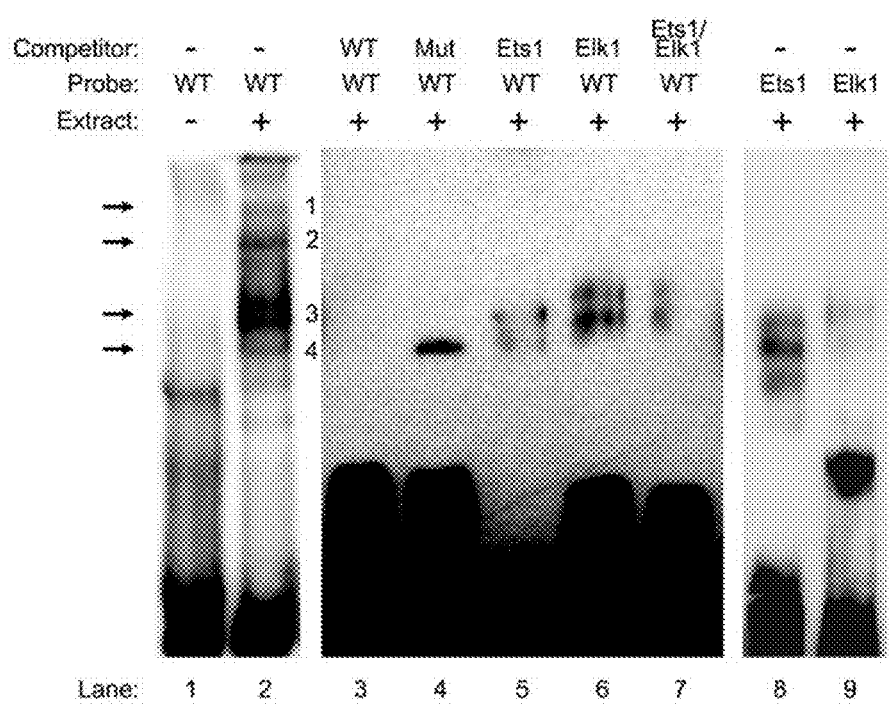
FIG. 13 depicts the in vitro binding of Ets1 and Elk1 to the proximal promoter region of the CIP2A gene. Electrophoretic mobility shift assay (EMSA) was performed with nuclear extracts (9 µg) ECC-1 cells that was incubated with the wild-type (WT) probe (−138 to −107) from human CIP2A gene as described in Materials and Methods. In competition experiments, a 100-fold molar excess of the designated probes were utilized to demonstrate the specificity of each binding reaction. Arrows indicate the formation of specific protein-DNA complexes. The experiment was repeated twice with similar results.

From ECC-1 cells, we next prepared nuclear extracts. As shown in FIG. 13, addition of the WT probe in the presence of nuclear extracts from ECC-1 cells displayed four (4) protein-DNA complexes (FIG. 13, lane 2). Competition with a 100-fold molar excess of unlabeled WT probe resulted in a complete inhibition of all four (4) protein-DNA complexes (FIG. 13, lane 3), indicating specificity. Competition with a 100-fold molar excess of unlabeled mutant probe, in which the palindromic binding sites for Ets1 and Elk1 were mutated, did not abolish the fourth protein-DNA complex, though the first three complexes were inhibited (FIG. 13, lane 4).

From these competition results, we speculated that it was the fourth DNA-protein complex that served as the binding site for Ets1 and Elk1. To confirm the loss of the fourth DNA-protein complex as the binding site for Ets1 and Elk1, a 100-fold excess molar competition was performed with the Ets1 and Elk1 consensus sequences. Addition of a 100-fold excess molar of Ets1 and Elk1 consensus sequences led to the loss of the fourth protein-DNA complex (FIG. 13, lanes 5-6).

Moreover, the pattern of protein-DNA complexes observed with the labeled Ets1 and Elk1 consensus probe were similar to those observed with the WT probe of the CIP2A gene (FIG. 13, compare lane 2 with lanes 8 and 9). These results indicate that the transcription factors Ets1 and Elk1 bind to the −138 to −107 region of the CIP2A gene and regulate its transcription in endometrial carcinoma cells.

Figure 14:
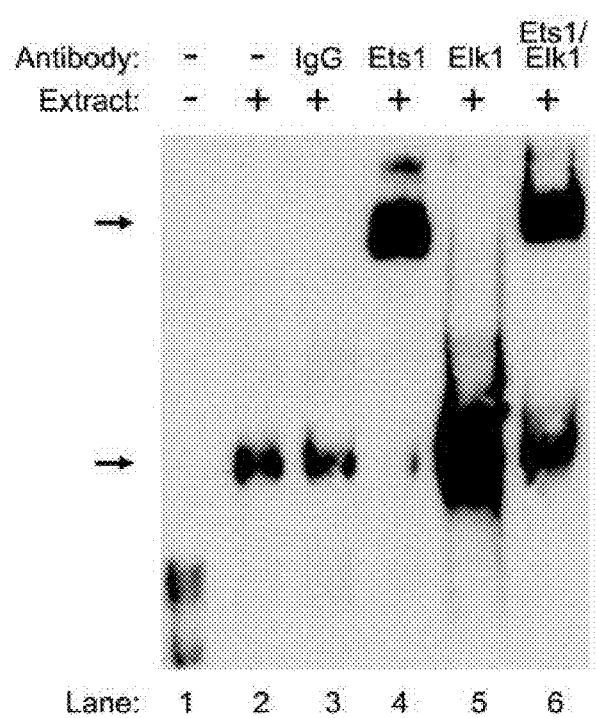
FIG. 14 depicts Ets1 and Elk1 binding to the proximal promoter of the CIP2A gene. Nuclear extracts (9 µg) from ECC-1 were incubated with WT probe (−138 to −107) from the CIP2A gene along with 5 µg of antibody directed towards Ets1, Elk1, or Ets1 and Elk1 together. The negative control consisted of rabbit-pre-immune control IgG. DNA-protein complex formations are designated by solid arrows.

In a separate series of experiments, we performed a gel-super shift analysis to further confirm our results. As a negative control, pre-immune IgG was utilized (FIG. 14, lane 3) and no shift was detected. Addition of Ets1 antibody to the nuclear extract from ECC-1 cells in the presence of the WT probe caused a shift in the protein DNA complex (FIG. 14, lane 4). Interestingly, in the presence of Elk1 antibody, the intensity of the protein-DNA complex was greatly enhanced rather than a shift (FIG. 14, lane 5). In the presence of both Ets1 and Elk1 antibodies, we detected a shift and an increase in the intensity of the protein-DNA complex (FIG. 14, lane 6). These gel-shift assay results further confirm that Ets1 and Elk1 bind to the palindromic sequence (−138 to −107) of the CIP2A promoter.

All together, these studies show the in vitro binding of Ets1 and Elk1 transcription proteins to the CIP2A proximal promoter region.

Figure 15:
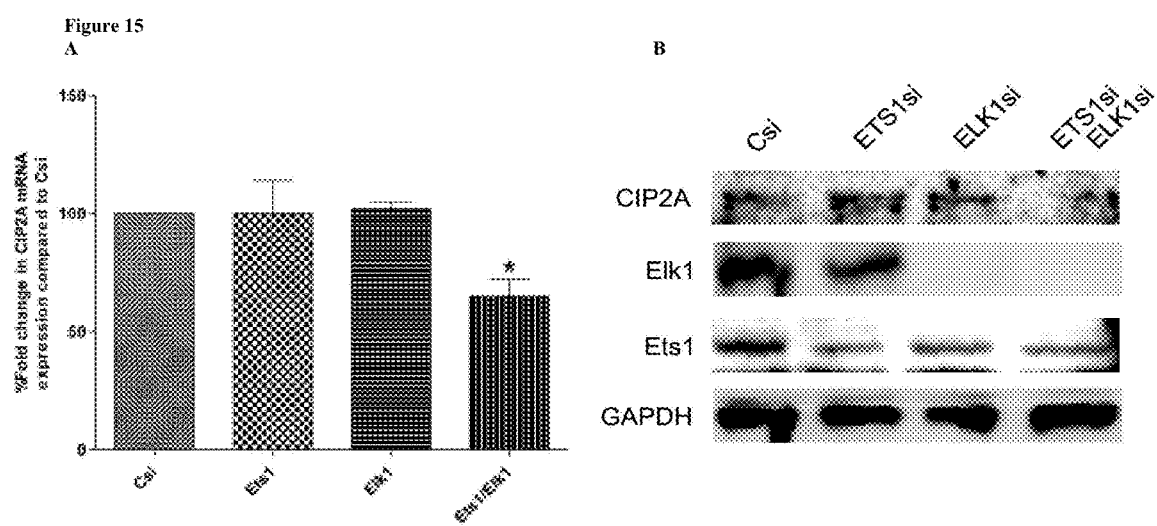
FIG. 15A depicts the effect of Ets1, Elk1 siRNA on CIP2A mRNA expression. HeLa cells were transiently transfected with 100 nM of Ets1 siRNA (SEQ ID NOs: 30, 31) or Elk1 (SEQ ID NOs: 32, 33) or Ets1/Elk1 (SEQ ID NOs: 30, 31, 32, 33) or siRNA-scramble as the negative control. The siRNA transfected cells showed a decrease in CIP2A mRNA expression levels.
FIG. 15B depicts the Western blot analysis of the HeLa cells transfected with siRNA against the Ets1 and Elk1 mRNA. siRNA treatment reduces CIP2A protein, without altering the GAPDH level, indicating specificity.

Example 8 siRNA-Targeted Reductions of Ets1 and Elk1 Leads to a Decrease in CIP2A mRNA Expression Our results from site-directed mutagenesis identified the Ets1/Elk1 palindromic binding sites within the ~200 bp CIP2A promoter essential for regulating CIP2A transcription in human cervical and endometrial carcinoma cells and demonstrated the in vitro association of Ets1/Elk1 binding to CIP2A gene promoter. In order to analyze directly the role of individual transcription factor(s) Ets1 or Elk1 in regulating the transcription of CIP2A gene, human cervical carcinoma cells were transfected with siRNA specific towards Ets1 (SEQ ID NO: 30, 31), Elk1 (SEQ ID NO: 32, 33) or Ets1/Elk1 together (Table 5). A significant 40% decrease in CIP2A mRNA expression levels was observed when HeLa cells were transfected with siRNA towards Ets1/Elk1 together, in contrast there was no significant effect in altering CIP2A mRNA expression levels when siRNA specific towards Ets1 or Elk1 was utilized (FIG. 15A). Moreover the specificity of siRNA utilized for knock-down of target gene was significant as there was a 3-fold decrease in Ets1 and Elk1 mRNA expression levels (FIG. 16) on treatment with siRNA specific for Ets1, Elk1 or Ets1/Elk1 together.

Additionally, in order to corroborate the results from knock-down studies the effect of siRNA on endogenous expression of CIP2A protein was analyzed in human cervical carcinoma cells (HeLa) cells 72 hours after transfection. As shown in FIG. 15B decreased CIP2A protein levels were observed with both Ets1/Elk1 together, while there was no change in CIP2A protein levels in the presence of either Ets1 or Elk1 individually. These results clearly demonstrate the direct role of Ets1/Elk1 together in regulating the basal transcription of CIP2A gene in human cervical carcinoma cells (HeLa).

In order to confirm if the CIP2A regulation by siRNA targeting Ets1 and Elk1 is cell type specific, we repeated the experiments using a different cell type (e.g., prostate cancer cells). We transfected a cocktail of siRNAs targeting against Ets1 into a human prostate carcinoma cell type (PC-3). The cocktail of siRNAs targeting Ets1 is composed of two (2) siRNA having nucleotide sequences set forth in SEQ ID NO: 30 and SEQ ID NO: 31.

Figure 17:
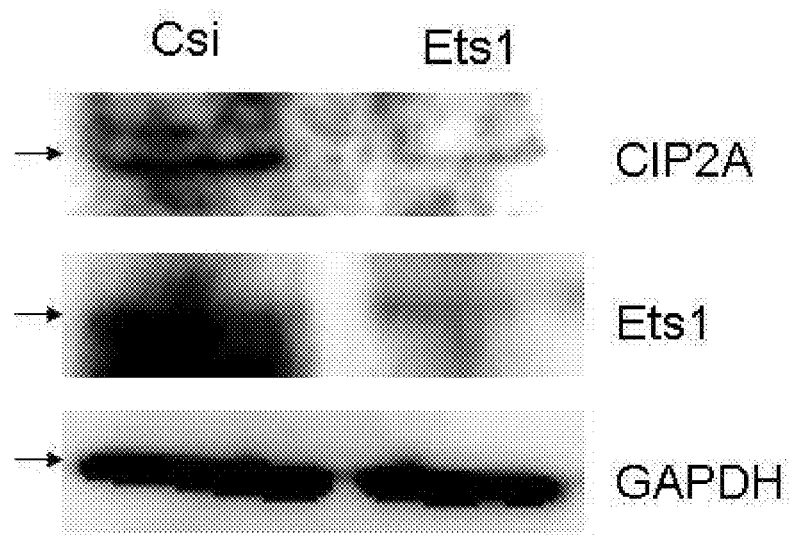
FIG. 17 depicts the effects of Ets1 siRNA on CIP2A protein expression in PC-3 (prostate cancer cells) in a Western blot analysis. GAPDH is used as a loading control. PC-3 cells were transiently transfected with 100 nM of Ets1 siRNAs (SEQ ID NO: 30 and SEQ ID NO: 31) or siRNA-scramble as the negative control (Csi; Dhramacon; catalog number: D-001206-13-20). The siRNA transfected cells showed a decrease in Ets1 protein expression as well as CIP2A protein expression.

As shown in FIG. 17, we observed a significant decrease in CIP2A protein expression in the PC-3 cells following siRNA treatment. These data indicate Ets1 alone is sufficient in regulating CIP2A in prostate cancer cells. The CIP2A regulation in prostate cancer cells and gastric cancer cells has been previously reported by Khanna et al. (2011) to require Ets1. Contrary to prostate cancer cells and gastric cancer cells, Ets1 alone is not sufficient in regulating CIP2A in cervical cancer cells or endometrial cells, but require both Ets1 and Elk1 (See, FIG. 15). Altogether, these data suggest CIP2A transcriptional regulation is cell type specific—while Ets1 alone regulates CIP2A in prostate and gastric cancer cells, both Ets1 and Elk1 are required in cervical and endometrial cancer cells.

Add-Back Studies—Specificity of Ets1 and Elk1 in Expression of CIP2A

Figure 18:
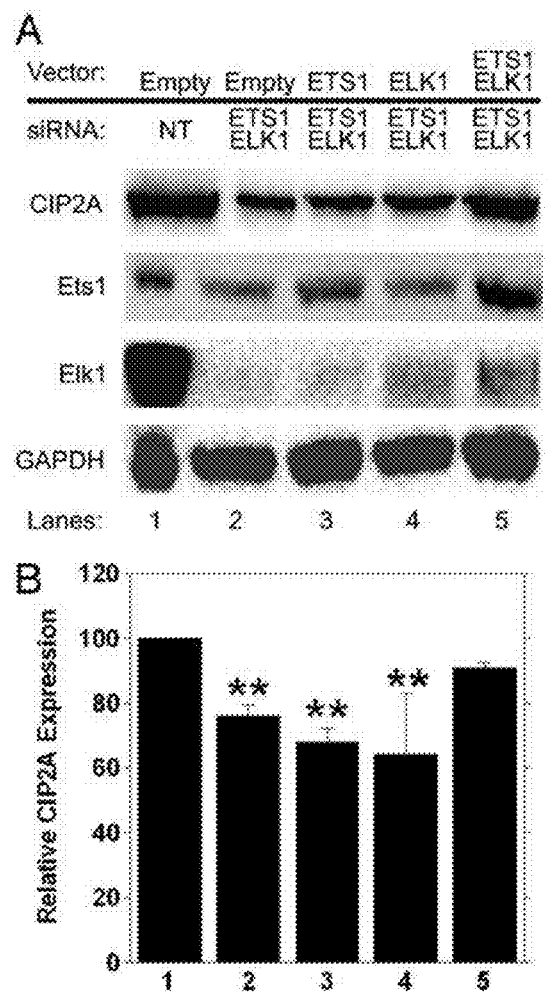
FIG. 18 depicts the ectopic expression of ETS1 and ELK1 together rescues CIP2A expression against 3'-UTR siRNA treatment. HeLa cells were transiently transfected with 100 nM of ETS1 and ELK1 3'-UTR siRNA together or non-targeting (NT) siRNA as the negative control. ETS1 and ELK1 cDNA were cloned into pCDN4-His Max Topo expression vector (Invitrogen, K864-20) utilizing the primers mentioned in Table 7, generating Ets1-Topo and Elk1-Topo. Sequences of the clones were verified and 1 µg was utilized for ectopic expression in HeLa cells following 3'-UTR siRNA treatment. Cells transfected with the empty vector served as a negative control. (A) Western blot analysis of CIP2A, Ets1, Elk1 and GAPDH protein expression levels were analyzed 72 hours after transfection and (B) qRT-PCR was conducted at 48 hours after transfection to confirm rescue of CIP2A mRNA **p<0.01.

To corroborate our observations, we completed an add-back assay to confirm the specificity for Ets1 and Elk1 in basal expression of CIP2A. In this series of studies, we transfected HeLa cells with either non-targeting siRNA (FIG. 18A, lane 1) or siRNA against the 3'-UTR regions of ETS1 and ELK1, effectively depleting the cells of endogenous Ets1 and Elk1 protein (FIG. 18A, lane 2).

The nucleotide sequences for the 3' UTR ETS1 are GGUUGGACUCUGAAUUUUG (SEQ ID NO: 64) that binds to the nucleotides 1599-1617 on the NM_001143820.1 (the disclosure of which is incorporated herein by reference). The nucleotide sequences for the 3' UTR ETS1 CCCCAAG-GUUAAAUACAA (SEQ ID NO: 65) that binds to the nucleotides 3166-3184 on the NM_001143820.1 (the disclosure of which is incorporated herein by reference). The nucleotide sequences for the 3' UTR ELK1 are GCGGUUUAUUUAU-UUAUUU (SEQ ID NO: 66) that binds to the nucleotide 1868-1886 on NM_991114123.1 (the disclosure of which is incorporated herein by reference). The nucleotide sequences for the 3' UTR ELK1 are CUGCCAUUUUGAUAGUAUA (SEQ ID NO: 67) that binds to the nucleotides 2420-2437 on NM_001114123.1 (the disclosure of which is incorporated herein by reference).

We co-transfected cells with either empty vector (FIG. 18A, lanes 1 and 2) or vectors over-expressing Ets1 gene or Elk1 gene or Ets1 and Elk1 genes together (FIG. 18A, lanes 3, 4, 5), which were resistant to Ets1 and Elk1 3'-UTR siRNA and analyzed cell lysates by western analysis. A significant decrease in CIP2A protein levels was observed in HeLa cells upon treatment with both Ets1 and Elk1 3'-UTR siRNA (FIG. 18A, lane 2) when compared to non-targeting siRNA (FIG. 18A, lane 1).

Furthermore ectopic expression of either Ets1 gene or Elk1 gene alone did not rescue CIP2A expression in HeLa cells (FIG. 18A, lanes 3, 4) treated with Ets1 and Elk1 3'-UTR siRNA. The loss of CIP2A protein was rescued in HeLa cells when Ets1 gene and Elk1 gene were over-expressed together (FIG. 18A, lane 5) in the presence of Ets1 and Elk1 3'-UTR siRNA. CIP2A mRNA was significantly decreased when cells were treated with Ets1 and Elk1 3-UTR siRNA (FIG. 18B, comparing column 1 and column 2), when analyzed by qRT-PCR, and CIP2A expression was not recovered when Ets1 gene or Elk1 gene were over-expressed individually (FIG. 18B, comparing column 3 and column 4 to column 1). CIP2A expression was returned to normal levels when both Ets1 gene and Elk1 gene were over-expressed (FIG. 18B, comparing column 5 to column 1). These results confirm the specificity of Ets1 and Elk1 transcription factors in regulating the basal transcription of CIP2A.

Example 9

In Vivo Association of Ets1 and Elk1 with the CIP2A Gene Promoter

Figure 19:
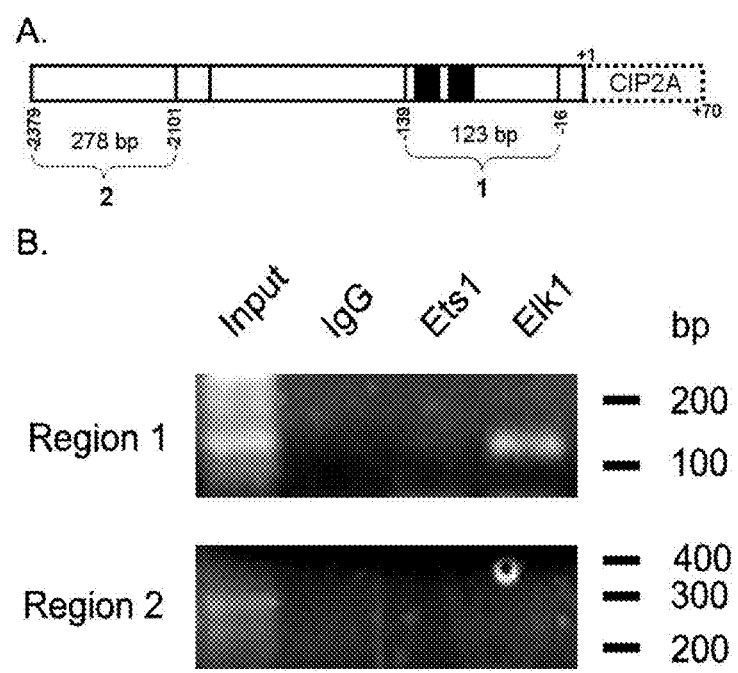
FIG. 19 depicts the ChIP analysis of Ets1 and Elk1 binding to the CIP2A promoter. (A) Schematic representation of the Ets1 and Elk1 binding sites within the CIP2A proximal promoter region. The primers utilized for amplification of DNA region are noted in Table 6. (B) ChIP analysis of the Ets1 and Elk1 association with the CIP2A promoter. Mouse IgG serves as a negative control. Region 1 is specific for a region containing the Ets1 and Elk1 binding sites in the CIP2A promoter, while region 2 is a distal part of the CIP2A gene which is devoid of the Ets1 and Elk1 binding sites.

To assess the in vivo association of Ets1 and Elk1 to the CIP2A gene promoter, a chromatin immunoprecipitation (ChIP) analysis was performed. The cross-linked protein-DNA was immunoprecipitated with antibodies against Ets1, Elk1. Mouse pre-immune IgG was used as a control. In a series of study, the amplification of a 123 bp fragment harboring the Ets1 and Elk1 binding sites within the CIP2A promoter was detected in the immunoprecipates obtained in HeLa cells when the Ets1 or Elk1 antibodies were used (FIG. 19B, region 1), while there was no amplification in the IgG control.

A second region was amplified that does not contain Ets1 or Elk1 binding sites in the CIP2A promoter, 2379 bp downstream of the ATG start site. The 278 bp fragment was visible in the input sample obtained from the HeLa cell line (FIG. 19B, region 2) while amplification was not seen in DNA obtained with antibody precipitation. These results demonstrate that the transcription factor(s) Ets1 and Elk1 associate with CIP2A gene promoter in HeLa cells.

In a separate series of study, we continued to confirm our in vitro data and have used chromatin immunoprecipitation (ChIP) analyses and quantitative PCR to assess the direct in vivo association of Ets1 and Elk1 with the CIP2A gene promoter. Cross-linked protein-DNA was immunoprecipitated with antibodies against Ets1, Elk1 or pre-immune IgG.

Figure 20:
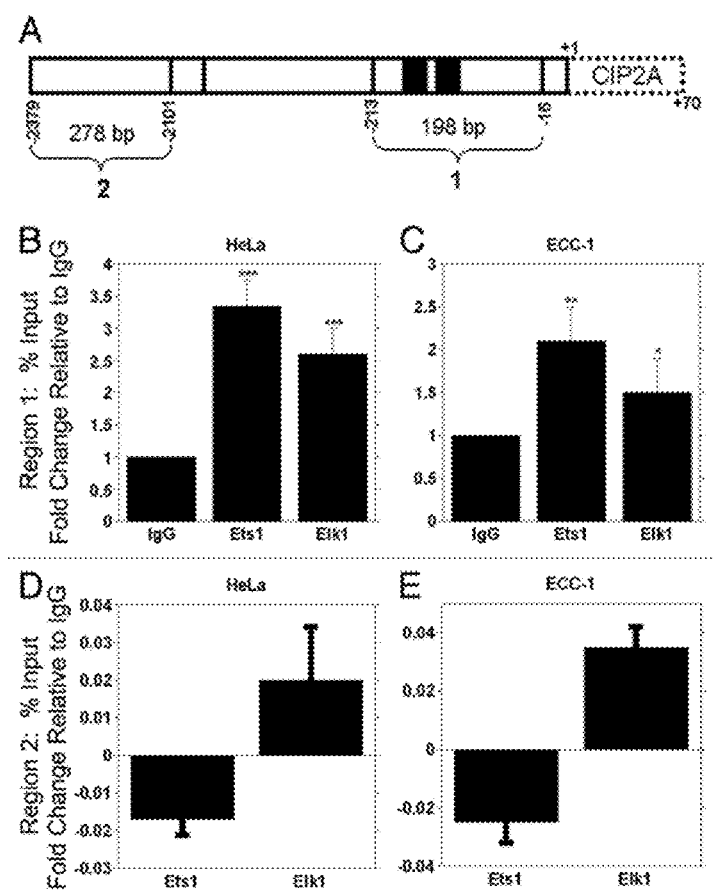
FIG. 20 depicts the ChIP analysis of Ets1 and Elk1 binding to the CIP2A promoter. (A) Schematic representation of the Ets1 and Elk1 binding sites within the proximal promoter region. The primers utilized for amplification of DNA region are noted in Table 4. ChIP qPCR analysis of Ets1 and Elk1 association with the CIP2A promoter for region 1 in (B) HeLa and (C) ECC-1 and region 2 for (D) HeLa and (E) ECC-1 are shown. Mouse IgG serves as a negative control. Region 1 is specific for the region containing the Ets1 and Elk1 binding sites in the CIP2A promoter, while region 2 is a distal part of the CIP2A gene which is devoid of Ets1 and Elk1 binding sites. The fold enrichment from IgG, Ets1 and Elk1 immunoprecipitation are shown and were calculated relative to input as % input. The fold change in occupancy was calculated by setting the fold enrichment of IgG to 1. The results are from two different experiments, each experiment performed in duplicate (*p<0.001, p<0.01, *p<0.05 with Ets1, Elk1 compared to the control IgG).

We used two primer sets to examine the specificity of Ets1 and Elk1 binding (FIG. 20A). Region 1 contains the two binding sites for Ets1 and Elk1, while region 2 has no binding sites for the transcription factors. We found that Ets1 immunoprecipitation (IP) resulted in a significant 3-fold increase in binding to the CIP2A promoter at region 1, while IP with the Elk1 antibody resulted in a significant 2-fold increase in binding to the CIP2A promoter compared to IgG in HeLa cells (FIG. 20B). Similarly Ets1 and Elk1 IP from ECC-1 cells showed a significant 2-fold increase in binding to CIP2A promoter occupancy compared to control IgG (FIG. 20C). In contrast, the Ets1 and Elk1 immunoprecipitates did not amplify CIP2A promoter fragment in the region between −2379 to −2101 in either cell lines. These results demonstrate that Ets1 and Elk1 associate with CIP2A gene promoter in vivo in cervical and endometrial carcinoma cells.

Example 10

Expression Levels of CIP2A, Ets1, and Elk1 in Human Cervical Patient Samples

Figure 21:
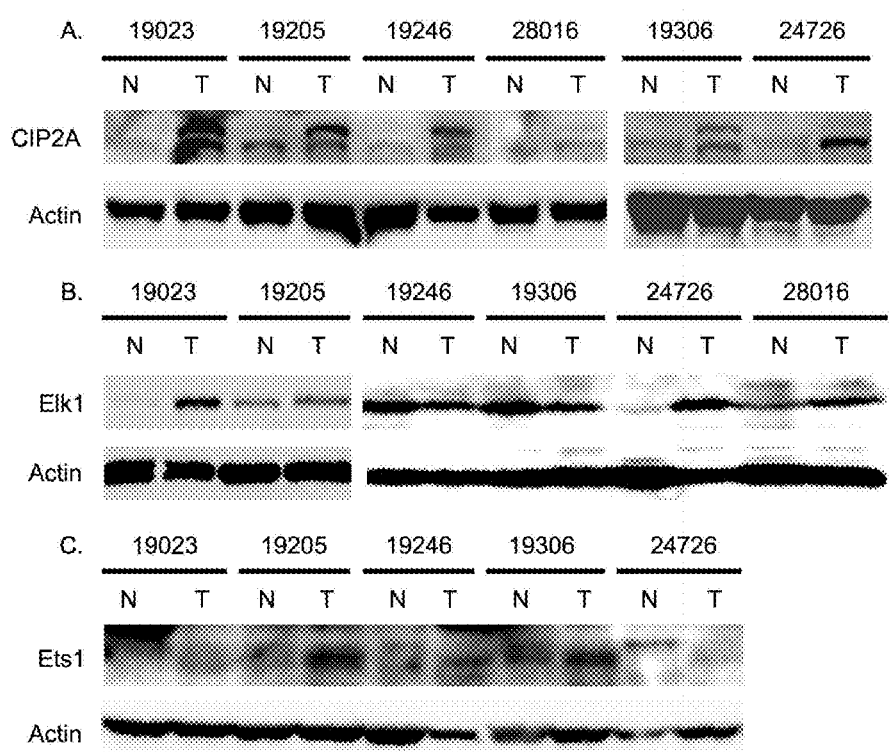
FIG. 21 depicts the CIP2A, Ets1 and Elk1 protein expression levels in human cervical tumor samples. Six (6) different matched pair of human cervical tumor samples (T) with adjacent normal tissue (N) were obtained and used in this series of experiments. Protein extraction was performed using protocol as described in Experimental Methods and Protocols. CIP2A, Ets1 and Elk1 protein expression were monitored using Western blot analysis. Patient pathological characteristics of patient cervical carcinoma tissue samples were described in Table 1. The protein expression levels of (A) CIP2A, (B) Elk1, (C) Ets1 and Actin (i.e., β-actin; used as a loading control) were monitored by western blotting.

To correlate our findings in human cervical patient samples, six (6) matched pairs of cervical tumor and normal adjacent tissue (NAT) were purchased. The protein levels of CIP2A, Ets1, Elk1 and Actin were identified via Western blot analysis. Increased expression of CIP2A protein levels were observed in all six tumor samples compared to the NAT samples (FIG. 21A). Similarly, four (4) of the tumor samples showed an increase in Elk1 (FIG. 21B) and Ets1 (FIG. 21C) protein levels when compared to NAT samples. In all tumor samples, Ets1, Elk1, or both were over-expressed. Together, these results substantiate the observation that Ets1 and Elk1 regulate the basal transcription of CIP2A in human cervical tumors.

Experimental Methods and Protocols

A) Cell Culture

The human cervical carcinoma cell line HeLa was grown in DMEM supplemented with 10% fetal calf serum (Invitrogen, Carlsbad, Calif.) and penicillin-streptomycin (Sigma, St. Louis, Mo.) at a final concentration of 100 µg/ml. The hepatocellular carcinoma cells HepG2 were maintained in DMEM with 10% FCS and 10 µg/ml gentamicin (Invitrogen, Carlsbad, Calif.). The endometrial carcinoma cells ECC-1 were grown in RPMI-1640 supplemented with 5% FCS (Invitrogen, Carlsbad, Calif.). All cells were grown at 37° C. in a 5% $CO_2$ incubator.

B) Human Cervical Carcinoma Tissue Samples

Six matched pair of human cervical carcinoma tissue samples were purchased from ILS Bio, LLC (Chestertown, Md.). These tissue samples were analyzed for their protein expression levels of CIP2A, Ets1, and Elk1. The description of the tissue sample is provided in Table 1.

C) Construction of CIP2A Luciferase Reporter Vector and 5' Deletion Analysis

The BAC clone RP11-161J9 (Rosewell Parker Cancer Institute Human BAC library) harboring the 5' flanking region of CIP2A gene (GenBank accession no AC092693.8) was utilized to design the primers for construction of CIP2A promoter-luciferase plasmids. DNA isolated from HeLa cells were utilized as templates to generate PCR fragments using Taq polymerase (Takara), which were further cloned into the reporter vector at the NheI-XhoI poly cloning sites by incorporating the corresponding restriction sties in the forward and reverse primers. The full length construct −2379/+70 luciferase promoter consists of approximately 2.4 kbp region upstream and 70 bp downstream of transcription start site (TSS) was cloned into the pGL4.10 [luc2] vector (Promega, Madison, Wis.). Similarly PCR amplified promoter regions −1452/+70, −941/+70, −428/+70, −284/+70, −213/+70, −171/+70, −123/+70 and −95/+70 were cloned in NheI-XhoI sites of pGL4-basic vector. The nucleotide sequence of the clones was verified by sequencing.

D) Transient Transfection and Luciferase Assay

Cells were seeded in 6-well plates at a density of $5\times10^5$ cells/well for HeLa, HepG2 and $8\times10^5$ for ECC-1 cells, 24 hours before transfection. Transfection was performed utilizing Lipofectamine 2000 reagent (Invitrogen) following manufactures recommendations. In each experiment, 2 µg of control vector (pGL4-basic without CIP2A promoter insert, empty vector) or the reporter vector (CIP2A full length promoter fragment or sequentially deleted CIP2A PCR fragments in pGL4-basic vector) was co-transfected along with 250 ng of pRL-TK (*Renilla* luciferase, Promega) as an internal control. Following incubation with DNA complex for 4 h cells were feed with 2 mL of fresh growth medium for an additional 44 hours. Luciferase assay was utilizing a 384 well robotic plate reader (EnVision, Perkin Elmer).

E) Identification of Potential Putative Transcription Factor Binding Sites in CIP2A Gene Promoter Potential transcription factor(s) binding sites within the CIP2A gene promoter was screened with the assistance of computer programs such as ALGEN-PROMO or ALIBABA 2.0 programs (www.gene-regulation.com).

F) Site-Directed Mutagenesis

The −171/+70 CIP2A promoter fragment was used to generate mutant clones of CIP2A promoter. The Quickchange lightning site-directed mutagenesis kit (Stratagene) was utilized to generate mutants CIP2A Mut1-CIP2A Mut6. Primers for introduction of point mutations or deletions were designed as instructed by the manufacturer. The nucleotide sequence of the mutated clones was verified by sequencing. The promoter activity of the mutated clones was assayed by transient transfection and luciferase assay as detailed in previous section.

G) Electrophoretic Mobility Shift Assay (EMSA) and Gel Super-Shift

Nuclear extracts were prepared from ECC-1 cells. $1\times10^7$ cells were seeded in 75 $cm^2$ flasks 24 h before nuclear proteins were extracted utilizing the nuclear complex CO—IP kit (Active Motif, 54001) as instructed by the manufacturer. The wild-type and the mutant probes were synthesized as double stranded oligonucleotides (Integrated DNA technology) from the −138 to −107 region of the CIP2A gene promoter. Consensus oligonucleotides for Ets1 and Elk1 were synthesized based on the sequence data from Santa Cruz Biotechnology (Santa Cruz, Calif.) and Panomics (Affymetrix, Calif.). The sequences of the probes utilized were: WT—5'-GACTTC-CGGAGCCCGACCGGATCCGGAAGCTT-3' (SEQ ID NO: 68); Mutant—5'-GAAAATTTAAGCCCGACCG-GATAAATTTACTT-3' (mutated bases shown in bold text) (SEQ ID NO: 69); Ets1—5'-GATCTCGAGCAGGAAGT-TCGA-3' (SEQ ID NO: 70); Elk1—5'-TTTGCAAAATG-CAGGAATTGTTTTCACAGT-3' (SEQ ID NO: 71). All the probes were labeled with biotin using the Biotin 3'-end DNA labeling kit (Thermo Scientific, 89818) according to the manual. Nine micrograms of the nuclear extract was utilized for the binding reactions. The EMSA binding reactions were performed at room temperature for 30 min and consisted of the nuclear extract in 1× binding buffer (50% glycerol, 100 mM $MgCl_2$, 1 μg/g1 Poly (dI-dC), 1% NP-40, 1 M KCl, 200 mM EDTA and 5 μM DNA probe). The mixture was run on 8% non-denaturing polyacrylamide gels in 0.5× Tris Borate-EDTA buffer at 170 V. The protein-DNA complexes were then transferred to Hybond-N+ nylon membrane using the Trans-Blot semi-dry method (Bio-Rad, CA) and cross-linked using the Spectrolinker XL-1000 UV crosslinker (Spectronics Corporation, N.Y.). Detection of biotin-labeled DNA was performed using the LightShift chemiluminsecent EMSA kit (Thermo Scientific, 20148) and visualized by exposure to a charge-couple device camera (GE ImageQuant LAS 4000).

For competition EMSA, 100-fold molar excess of the cold, mutant or consensus oligonucleotide was added to the EMSA binding reaction. For the gel-Supershift assay, following the incubation of the nuclear extracts with the 32 bp WT CIP2A promoter fragment for 30 min, 5 μg of Ets1 antibody (Abcam, ab124282), 5 μg of Elk1 antibody (Epitomics, 1277-1) and/or the two antibodies (anti-Ets1 and Elk1) were added to the binding reaction and the mixture incubated at RT for an additional 30 min. The pre-immune IgG (Millipore, 12-371) was utilized as negative control in the Supershift assay. The mixture was fractionated on 5% non-denaturing polyacrylamide gel. Transfer and detection was performed as described above.

H) Ets1/Elk1 siRNA Knockdown, Overexpression and CIP2A Expression Analysis

In order to assess the direct effect of Ets1/Elk1 in regulating the transcription of CIP2A gene promoter, human siRNA specific towards (i.e., targeted against) Ets1 (Dharmacon, Lafayette, Colo.; J-003887-06, J-003887-08), Elk1 (Dhramacon, Lafayette, Colo.; J-003885-06, J-003885-08) or Ets1/Elk1 together were utilized. siGENOME non-targeting siRNA pool 1 (Dharmacon, D-001206-13) was used as negative control. Human cervical carcinoma cell line HeLa were seeded at a density of $5\times10^5$ cells/well were transiently transfected with 100 nM of each of the targeted siRNA or in combination utilizing Lipofectamine 2000 (Invitrogen). RNA and protein were isolated 24 hours and 72 hours after transfection for CIP2A expression levels.

One microgram (1 μg) of the RNA was used in the reverse transcription reaction along with 4 U of Omniscript reverse transcriptase (Qiagen, Valencia, Calif.), 1 μM oligo-dT primer (Qiagen), 0.5 mM dNTP (Qiagen), 10 U of RNase inhibitor (Qiagen) and 1×RT buffer (Qiagen). Reverse transcription was performed at 37° C. for 1 hour with a final incubation at 93° C. for 5 min for inactivation of reverse transcriptase. Two microliters (2 μl) of the RT-product was used in the real time PCR reaction. The Quantitect SYBR green PCR kit (Qiagen) was utilized and PCR was performed according to the manufacturer's instructions using the Stratagene MXPRO 3000 real time RT cycler (Agilent Technologies, Santa Clara, Calif.). Each PCR reaction consisted of 50% (v/v) of 2×SYBR green master mixes and 0.2 μM gene-specific forward and reverse primers. Quantification of glyceraldehyde-6-phosphate dehydrogenase (GADPH) was used to normalize the relative expression levels of CIP2A, Ets1 and Elk1 mRNA. Each experiment was performed in duplicates and repeated at least twice. The primer sequences used for qPCR are as follows:

(i) CIP2A:

(SEQ ID NO: 48)
    Forward: TGCCTGCTTGAAGTCCTTG (SEQ ID NO: 49)
    Reverse: TAGTCGTGTGAGTTTCTGTCC (ii) GAPDH:

(SEQ ID NO: 50)
    Forward: TGGGCTACACTGAGCACCAG (SEQ ID NO: 51)
    Reverse: GGGTGTCGCTGTTGAAGTCA (iii) Ets1: Qiagen product no: PPH01781B
(iv) Elk1: Qiagen product no: PPH00140B For the siRNA rescue experiment, $5\times10^5$ HeLa cells seeded in 6 well plates were transiently transfected with ETS1 3'-UTR siRNA and ELK1 3'-UTR siRNA (Dharmacon). siGENOME non-targeting siRNA pool 1 (Dharmacon) was utilized as the negative control. Transfections were performed with 100 nM of the targeted 3'-UTR siRNA in combination or the non-targeting pool with Lipofectamine RNAiMax (Invitrogen) as described by the manufacturer. Forty-eight hours after 3'-UTR siRNA treatment, cells were transiently transfected with 1 μg of Ets1-Topo and Elk1-Topo mammalian expression vector encoding respective cDNAs utilizing Lipofectamine RNAiMax (Invitrogen). HeLa cells transfected with empty vector served as a negative control. Protein was extracted 72 h after transfection for CIP2A analysis. Rabbit anti-CIP2A (Novus, NB100-68264), rabbit anti-Ets1 (Abcam, ab124282), rabbit-anti-Elk1 (Epitomics, 1277-1) and rabbit anti-GAPDH (Abcam, ab9385) were utilized for western blotting.

(I) Chromatin Immunoprecipitation Assay (ChIP Assay)

Chromatin immunoprecipitation was performed using $1-2\times10^7$ HeLa or ECC-1 cells, which were treated with 37% formaldehyde (Sigma, F1635) at 1% final concentration, vol/vol for 10 min at room temperature to cross-link proteins to DNA. After cross-linking the cells were washed twice with 1× ice-cold PBS containing protease inhibitor cocktail (Sigma, P8340). The cells were collected and centrifuged at 700×g for 2 min, re-suspended in 1 ml of SDS-lysis buffer with protease inhibitor cocktail. The cells were then sonicated twice with a bioruptor (Diagenode, UCD200) at high power, with 30 s on/off pulse for 15 mins (break up DNA to ~500 bp fragments). The cell lysate was centrifuged at 10,000×g for 15 min at 4° C. and the supernatant was further subjected to enzymatic digestion utilizing micrococcal nuclease (New England Biolabs, M0247) for 15 mins at 37° C. The enzyme activity was inactivated by adding 0.5 M ETDA and incubated on ice for 10 mins. 25 μl of the DNA fraction was kept aside as input for PCR. The remaining DNA fraction was precleared using a mixture of 35 μl of protein G and protein A agarose beads each (50% slurry, Millipore, 16-201, 16-157) for 2 hours at 4° C.

Immunoprecipitation was performed by adding antibodies towards Ets1 (Abcam, ab124282), Elk1 (Epitomics, 1277-1) or mouse IgG (Millipore, 12-371) as the negative control. The immunocomplex was precipitated by incubation with 70 μl of protein A/G agarose beads for 2 h at 4° C. The protein/DNA complex was eluted using 200 μl of elution buffer (1% SDS, 0.1 M NaHCO$_3$) from the beads. Cross-linking of protein-DNA was reversed by adding 10 μl of 5 M NaCl at 65° C. for 2-3 hours. The DNA was purified using spin columns (Promega, A9281) and 5 μl of the DNA was used in the qPCR reaction for amplification of 198 bp or 298 bp of the CIP2A promoter region (FIG. 5A). qPCR reactions were performed utilizing the primers in Table 6.

(J) Western Blot Analysis

Protein was isolated from cells, by initially washing the cells in 1× ice-cold PBS and re-suspending the cells in 250 μl of RIPA buffer supplemented with protease inhibitor cocktail (Sigma). Fifty microgram (50 μg) of protein was fractioned on 10% or 12% SDS-PAGE and transferred to nitrocellulose membrane, blocked at 4° C. overnight in 5% non-fat milk in TBS and incubated with rabbit anti-CIP2A (Novus), rabbit anti-Elk1 (Cell Signaling, Danvers, Mass.), rabbit anti-Ets1 (Millipore, Billerica, Calif.) and rabbit anti-GAPDH (Abcam, Cambridge, Mass.) at 4° C. overnight. Blots were washed with 1×TBST and incubated with anti-rabbit secondary HRP at room temperature for 1 hour. Detection of signal was performed by adding chemiluminsecent substrate (Pierce, Rockford, Ill.) and visualized by exposure to a charge-couple device camera (GE ImageQuant LAS 4000, Piscataway, N.J.).

(K) Statistical Analysis

Statistical analysis was performed for calculating the significant differences in luciferase activity between constructs, effect of siRNA in knock-down of CIP2A mRNA expression and effect of Ets1, Elk1 overexpression in CIP2A mRNA by one way randomized analysis of variance (ANOVA) and Newam-Keuls test with significance level of $p<0.05$.

All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments.

REFERENCES

Hoo L S, Zhang J Y, Chan E K L. Cloning and characterization of a novel 90 kDa companion auto-antigen of p62 overexpressed in cancer. *Oncogene* 2002; 21:5006-15.

Li W, Ge Z, Liu C, Liu Z, Bjorkholm M, Jia J, Xu D. CIP2A is overexpressed in gastric cancer and its depletion leads to impaired clonogenicity, senescence or differentiation of tumor cells. *Clin Cancer Res* 2008; 14: 3722-28.

Côme C, Laine A, Chanrion M, Edgren H, Mattila E, Liu X, Jonkers J, Ivaska J, Isola J, Darbon J M, Kallioniemi O, Thézenas S, Westermarck J. CIP2A is associated with human breast cancer agressivity. *Clin Cancer Res* 2009; 15: 5092-100.

Khanna A, Böckelman C, Hemmes A, Junttila M R, Wiksten J P, Lundin M, Junnila S, Murphy D J, Evan G I, Haglund C, Westermarck J, Ristimäki A. MYC-dependent regulation and prognostic role of CIP2A in gastric cancer. *J Natl Cancer Inst* 2009; 101: 793-805.

Katz J, Jakymiw A, Ducksworth M K, Stewart C M, Bhattacharyya I, Cha S, Chan E K L. CIP2A expression and localization in oral carcinoma and dysplasia. *Cancer Biol Ther* 2010; 10: 694-99.

Vaarala M, Väisänen MR, Ristimäki A. CIP2A expression is increased in prostate cancer. *J Exp Clin Cancer Res* 2010; 29: 136-39.

Liu, J, Wang X, Zhou G, Wang H, Xiang L, Cheng Y, Liu W, Wang Y, Jia J, Zhao W. Cancerous inhibitor of protein phosphatase 2A is overexpressed in cervical cancer and upregulated by human paillomavirus 16 E7 oncoprotein. *Gynecol Oncol* 2011; 122: 430-36.

Qu W, Li W, Wei L, Xing L, Wang X, Yu J. CIP2A is overexpressed in esophageal squamous cell carcinoma. *Med Oncol* 2010:1-6. (DOI 10.1007/s12032-010-9768-9).

Dong Q Z, Wang Y, Dong X J, Li Z X, Tang Z P, Cui Q Z, Wang E H. CIP2A is overexpressed in non-small cell lung cancer and correlates with poor prognosis. *Ann Surg Oncol* 2011; 18: 857-65.

Lucas C M, Harris R J, Giannoudis A, Copland M, Slupsky J R, Clark R E. Cancerous inhibitor of PP2A (CIP2A) at diagnosis of chronic myeloid leukemia is a critical determinant of disease progression. *Blood* 2011; 117: 6660-68.

Wang J, Li W, Li L, Yu X, Jia J, Chen C. CIP2A is overexpressed in acute myeloid leukemia and associated with HL60 cells proliferation and differentiation. *Int Jnl Lab Hem* 2011; 33: 290-98.

Lee J, Park E J, Hwang J W, Oh J M, Kim H, Bae E K, Choi Y L, Han J, Ahn J K, Cha H S, Koh E M. CIP2A expression is associated with synovial hyperplasia and invasive function of fibroblast-like synoviocytes in rheumatoid arthritis. *Rheumatol Int* 2011. (DOI 10.1007/s00296-011-1927-6).

TABLE 1

Pathological Characteristics of Human Cervical Carcinoma Tissue Samples

| Identification No. | Cervical Cancer Phenotype | Donor Race |
| --- | --- | --- |
| 19203 N | | Georgian |
| 19203 D | Undifferentiated Carcinoma Grade III | Georgian |
| 19306 N | | Georgian |
| 19306 D | Adenosquamous Cell Carcinoma Grade II | Georgian |
| 19205 N | | Georgian |
| 19205 D | Squamous Cell Carcinoma (SSC) Grade II | Georgian |
| 19246 N | | Georgian |
| 19246 D | Squamous Cell Carcinoma (SSC) Grade II | Georgian |
| 24726 N | | Vietnamese |
| 24726 D | Adenocarcinoma Grade III | Vietnamese |
| 28016 N | | Vietnamese |
| 28016 D | Adenocarcinoma Grade III | Vietnamese |

N is normal subject; D is disease subject.

TABLE 2

Identification of Human CIP2A Basal Proximal Promoter

| 5' Deletion Construct | Fold increase in Relative luciferase activity (RLA) | | |
| --- | --- | --- | --- |
| | HeLa | HepG2 | ECC-1 |
| pGL4 Basic | 1 | 1 | 1 |
| CIP2A −95/+70 | 0.4 | 0.4 | 5.3 |
| CIP2A −123/+70 | 11.0 | 1.8 | 71.0 |
| CIP2A −171/+70 | 57.0 | 5.0 | 208.0 |
| CIP2A −213/+70 | 39.0 | 4.0 | — |
| CIP2A −284/+70 | 54.0 | 6.0 | — |
| CIP2A −428/+70 | 58.0 | 12.0 | 210.0 |
| CIP2A −941/+70 | 253.0 | 30.0 | 426.0 |
| CIP2A −1452/+70 | 63.0 | 6.0 | — |
| CIP2A −2379/+70 | 65.0 | 4.0 | 134.0 |

Human cervical carcinoma cells (HeLa), liver hepatoblastoma cells (HepG2), and endometrial carcinoma cells (ECC-1) were transfected with various CIP2A promoter constructs. Luciferase activity was assayed 48 hours after transfection. Fold increase in relative luciferase activity (RLA) was compared with pGL4 basic (value set as 1). Normalization in transfection efficiency was performed by co-transfection with pRL-TK (*Renilla* expression vector). Mean ± S.D. are from three different experiments, each performed in triplicate.

TABLE 3

Primer Sequences Utilized for CIP2A 5' Deletion Clones

| SEQ ID NO | CIP2A clone | Forward Primer | Reverser Primer |
|---|---|---|---|
| 1 | CIP2A −2379/+70 (SEQ ID NO: 1) | 5'-GCTAGCaaactggaaattaaaagcgtgagc-3' (SEQ ID NO: 10) | 5'-CTCGAGcctctgacttcacggctttgt-3' (SEQ ID NO: 11) |
| 2 | CIP2A −1452/+70 (SEQ ID NO: 2) | 5'-GCTAGCctcccttggccagattttacctaat-3' (SEQ ID NO: 12) | 5'-CTCGAGcctctgacttcacggctttgt-3' (SEQ ID NO: 13) |
| 3 | CIP2A −941/+70 (SEQ ID NO: 3) | 5'-GCTAGCtacaatttctacatcctggtttttaaagc-3' (SEQ ID NO: 14) | 5'-CTCGAGcctctgacttcacggctttgt-3' (SEQ ID NO: 15) |
| 4 | CIP2A −428/+70 (SEQ ID NO: 4) | 5'-GCTAGCagaggatgacgcacaaacgaaaaa-3' (SEQ ID NO: 16) | 5'-CTCGAGcctctgacttcacggctttgt-3' (SEQ ID NO: 17) |
| 5 | CIP2A −284/+70 (SEQ ID NO: 5) | 5'-GCTAGCgggatctcaggccgaaaa-3' (SEQ ID NO: 18) | 5'-CTCGAGcctctgacttcacggctttgt-3' (SEQ ID NO: 19) |
| 6 | CIP2A −213/+70 (SEQ ID NO: 6) | 5'-GCTAGCtcctggacccacaaatcacct-3' (SEQ ID NO: 20) | 5'-CTCGAGcctctgacttcacggctttgt-3' (SEQ ID NO: 21) |
| 7 | CIP2A −171/+70 (SEQ ID NO: 7) | 5'-GCTAGCcgtcaccgagaacggtc-3' (SEQ ID NO: 22) | 5'-CTCGAGcctctgacttcacggctttgt-3' (SEQ ID NO: 23) |
| 8 | CIP2A −123/+70 (SEQ ID NO: 8) | 5'-GCTAGCaccggatccggaagctt-3' (SEQ ID NO: 24) | 5'-CTCGAGcctctgacttcacggctttgt-3' (SEQ ID NO: 25) |
| 9 | CIP2A −95/+70 (SEQ ID NO: 9) | 5'-GCTAGCggggtggggccgaaaatcaaa-3' (SEQ ID NO: 26) | 5'-CTCGAGcctctgacttcacggctttgt-3' (SEQ ID NO: 27) |

Restriction sites NheI in the forward primer and XhoI in the reverse primer are indicated in bold.

TABLE 4

Primer Sequences Utilized For Sequencing

| SEQ ID NO | SEQUENCE NAME | SEQUENCE POSITION IN pGL4.10 [luc2] | SEQUENCE |
|---|---|---|---|
| 28 | RV primer 3 | 4191-4210 | 5'-ctagcaaaataggctgtccc-3' (SEQ ID NO: 28) |
| 29 | RV primer 4 | 2076-2095 | 5'-gacgatagtcatgccccgcg-3' (SEQ ID NO: 29) |

TABLE 5 siRNA Oligonucleotides Utilized for Ets1 and Elk1 Knock-Down

| SEQ ID NO | Target | siRNA oligonucleotide | Complimentary Region on Ets1 and Elk1 mRNA Accession No. |
|---|---|---|---|
| 30 | Ets1 | CAGAAUGACUACUUUGCUA (SEQ ID NO: 30) | CAGAATGACTACTTTGCTA NM 001143820.1-875-893 (Variant 1) (SEQ ID NO: 34) CAGAATGACTACTTTGCTA NM 005238.3-974-992 (Variant 2) (SEQ ID NO: 35) |
| 31 | Ets1 | GAAAUGAUGUCUCAAGCAU (SEQ ID NO: 31) | GAAATGATGTCTCAAGCAT NM 001143820.1-344-362 (Variant 1) (SEQ ID NO: 36) GAAATGATGTCTCAAGCAT NM 005238.3-443-461 (Variant 2) (SEQ ID NO: 37) |
| 32 | Elk1 | GCAGCAGCCGGAACGAGUA (SEQ ID NO: 32) | GCAGCAGCCGGAACGAGTA NM 001114123.1-762-780 (Variant 1) (SEQ ID NO: 38) GCAGCAGCCGGAACGAGTA NM005229.3-656-674 (Variant 2) (SEQ ID NO: 39) |

TABLE 5-continued siRNA Oligonucleotides Utilized for Ets1 and Elk1 Knock-Down

| SEQ ID NO: | Target | siRNA oligonucleotide | Complimentary Region on Ets1 and Elk1 mRNA Accession No. |
|---|---|---|---|
| 33 | Elk1 | CGGAAGAGCUUAAUGUGGA (SEQ ID NO: 33) | CGGAAGAGCTTAATGTGGA NM_001114123.1-1014-1032 (Variant 1) (SEQ ID NO: 40) CGGAAGAGCTTAATGTGGA NM005229.3-908-926 (Variant 2) (SEQ ID NO: 41) |

TABLE 6

Primers Used in Chromatin Immunoprecipitation

| REGION SPANNING CIP2A PROMOTER | NUCLEOTIDE SEQUENCE |
|---|---|
| −16 to −139 (within the CIP2A proximal promoter, which has the Ets1, Elk1 palindromic binding sites) (SEQ ID NO: 42) | Forward: GGACTTCCGGAGCCCGACCG (SEQ ID NO: 44) Reverse: CCGGCTTAGGGACCACCACCG (SEQ ID NO: 45) |
| −2101 to −2379 (distal region in the CIP2A promoter, which doesn't have the Ets1, Elk1 binding sites) (SEQ ID NO: 43) | Forward: AAACTGGAAATTAAAAGCGTGAGC (SEQ ID NO: 46) Reverse: TGCCATCTTTGTTGGATTTTGACTTA (SEQ ID NO: 47) |

TABLE 7

Primers Utilized for Construction of Ets1, Elk1 Mammalian Expression Vectors

| SEQUENCE NO. | CLONE | PRIMER SEQUENCE |
|---|---|---|
| SEQ ID NO: 52 (corresponds to NM_001143820.1) | Ets1-Topo | Forward: ATGAGCTACTTTGTGGATTCTGCTG (SEQ ID NO: 53) Reverse: TCACTCGTCGGCATCTGGCTTGACGTCCAG (SEQ ID NO: 54) |
| SEQ ID NO: 55 (corresponds to NM_001114123.2 or NM_005229.4) | Elk1-Topo | Forward: ATGGACCCATCTGTG (SEQ ID NO: 56) Reverse: TCATGGCTTCTGGGGCCCTGGGGAGAGCAC (SEQ ID NO: 57) |

The nucleotide sequences of NM_001143820.1, NM_001114123.2 and NM_005229.4 (publically available on NCBI's database) are expressly herein incorporated by reference.

---

What is claimed is:

1. A method of inhibiting gene expression of CIP2A in a cell, comprising the steps of:
   (i) providing a cell selected from the group consisting of liver cancer cell, endometrial cancer cell and cervical cancer cell;
   (ii) providing a first siRNA targeted against Ets1 mRNA, said first siRNA hybridizes to a target sequence of Ets1 mRNA selected from the group consisting of SEQ ID NO: 34, SEQ ID NO: 35, SEQ ID NO: 36 and SEQ ID NO: 37;
   (iii) providing a second siRNA targeted against Elk1 mRNA, said second siRNA hybridizes to a target sequence of Elk1 mRNA selected from the group consisting of SEQ ID NO: 38, SEQ ID NO: 39, SEQ ID NO: 40 and SEQ ID NO: 41; and
   (iv) exposing said first siRNA and said second siRNA to said cell, wherein said first siRNA and said second siRNA together inhibit the gene expression of CIP2A in said cell.

2. The method of claim 1, wherein said first siRNA is at least one siRNA selected from the group consisting of SEQ ID NO: 30 and SEQ ID NO: 31.

3. The method of claim 1, wherein said second siRNA is at least one siRNA selected from the group consisting of SEQ ID NO: 32 and SEQ ID NO: 33.

4. A method for inhibiting gene expression of CIP2A in a cell in vitro, said method comprising the steps of:
   (a) introducing into a cell a first siRNA, said cell is selected from the group consisting of liver cancer cell, endometrial cancer cell and cervical cancer cell, wherein said first siRNA is at least one siRNA selected from the group consisting of SEQ ID NO: 30 and SEQ ID NO: 31;
   (b) introducing into said cell a second siRNA, wherein said second siRNA is at least one siRNA selected from the group consisting of SEQ ID NO: 32 and SEQ ID NO: 33; and
   (c) culturing said cell to inhibit gene expression of CIP2A, wherein said inhibition of gene expression of CIP2A is evidenced by a decrease in CIP2A mRNA transcript.

5. A method for inhibiting gene expression of CIP2A in a human in vivo, comprising the steps of:
   (i) providing a first siRNA targeted against Ets1 mRNA, said first siRNA hybridizes to a target sequence of Ets1 mRNA selected from the group consisting of SEQ ID NO: 34, SEQ ID NO: 35, SEQ ID NO: 36 and SEQ ID NO: 37;
   (ii) providing a second siRNA targeted against Elk1 mRNA, said second siRNA hybridizes to a target sequence of Elk1 mRNA selected from the group consisting of SEQ ID NO: 38, SEQ ID NO: 39, SEQ ID NO: 40 and SEQ ID NO: 41; and
   (iii) administering to a human an effective amount of said first siRNA targeted Ets1 mRNA and said second siRNA targeted against Elk1 mRNA, said human suffers from a cancer selected from the group consisting of liver cancer, endometrial cancer and cervical cancer, wherein said first siRNA and said second siRNA together inhibit said gene expression of CIP2A in said human.

6. The method of claim 5, wherein said first siRNA consists of a nucleotide sequence set forth in SEQ ID NO: 30 or SEQ ID NO: 31.

7. The method of claim 5, wherein said second siRNA consists of a nucleotide sequence set forth in SEQ ID NO: 32 or SEQ ID NO: 33.

8. The method of claim 5, wherein said human is suffering from cervical cancer or endometrial cancer.

* * * * *

SEQUENCE LISTING

<160> NUMBER OF SEQ ID NOS: 70

<210> SEQ ID NO 1
<211> LENGTH: 2449
<212> TYPE: DNA
<213> ORGANISM: Homo sapiens

<400> SEQUENCE: 1

```
aaactggaaa ttaaaagcgt gagccactgc tcctggcctc ctgctccttt tcttcccttt      60
ttgaggccta aaagtatgga ttggtgtttc tcaaattagg atatgcaagt atctctgatt     120
aaaaatgtca agacttatca cagctagaaa cgatccctct tactaaactt acaacatcaa     180
ttttggtgaa gattttttga gaaagacatt tgatattaat tacagaagag aatacaaaat     240
ttgtatgact gcttaagtca aaatccaaca aagatggcac tgatagcacg cagctttgcg     300
cattaccctg ggcctctgaa tggggacgat gctgacacat catcacagat gaaaagtcca     360
acactatcaa actctgatca cttcatttgc caatgaggca ctgactgtaa cactgagaac     420
ttaattatgc cagatgacag ctgacacttt acattaattc attttttaac catctccaag     480
accgtatagg acctcatctc tactcctctc ctcctcgttc tttctacact agccacatgg     540
catccttgtt tctggcatac agtatcccac tttagggtct ttctttgcca tttcctctat     600
ctaaaaacct tttcccatag aatatggctc cctttctcaa ctccttgaag catttcccca     660
aatgttgctt tcttaatgag gtcaccttcc catttccctt atcaattacc acattattc      720
```

```
tagagtaata acgtctattt ttctctttat atcattttcc ttacttattt attgtgttta    780
ttatttggtt ccctaccaaa atgtaagttg catgccagta gtattttttgt ttttttcact   840
gagtctattg tgtctagaaa agtgcttagc acattgtaga ttctcaatga actacttatt   900
gaatgaacag tcctatgaac caggtatctc ccttggccag atttttaccta atgaagattc  960
tgcagcagtg agaacttgcc tagagtcaca tcgtcaaagg tggagctaga atctgtaagc  1020
aacctggctc tctactcttt accactgctg catgttactg catggtgcct ctcatttatg  1080
tggtgaattt caaaagtact attttgtatg tttcccttac tagacagttc cctcgcagca  1140
ggggatacta cttcatctct gttccctgac tggcagtttc taacccatgt tacacgctct  1200
ataattgttt acggaatgaa tgaaagcata atgaacaca caagctaccc aaagattttt   1260
acatgaatgt cccaactggt taaatcattt ttatcttttca gatttaaact tttataaaaa  1320
acaaaaccaa aacaccaaac ctgtcttcaa aaatctagta attcaaaaaa attcttttga  1380
agtgaaaaaa catgatttct gataaacgat ttaattaaat ggaaatgtac cctattctta  1440
caatttctac atcctggttt ttaaagcttt attcgacgtt aggaaatatt aagcaaaaag  1500
ctccaaaacc agtaactgac tcgcttcatt acatacacat gcaataatat taagctatct  1560
ccgatttaaa aaacgcaaat aatagtgcca ttttcgtaga catcgagaat tataaaacaa  1620
tcaatcatgc cagagagaaa cagacacctt cacttacaaa aactgacgct aacgagtaac  1680
accctccgga gcaatacctg cccagggtc agcaggagg agtcttctcg aataaatgtg  1740
acaaatactt tggtcagggc atgactaatt tgccacataa tgccaatagg ttgactctga  1800
gaaactacca tccccgggca gaaggggcgg gtgtaggaga gatttaaaaa cgaggcccct  1860
cccaggccgc ctcaaaatct agggcccaag attcttctcc tcagagctcc tcaccgtgtc  1920
tagactaggg gcaagcgacc atttctcagg tagaggatga cgcacaaacg aaaaactggc  1980
catccaacat gaaggacgag gaagcgcacg aaatcagagc gcacagctga gtgaggaatc  2040
cccttctcc taaccgattc ctctcccgag aaatcgcgag atttctcgcc ttcacgggat  2100
ctcaggccga aaacctcgcg gcctctcaga cgagggtggg ttagcggggg cagctcccaa  2160
cccccgtcct ggaccacaa atcacctcga cccctggccc accccggccg tcaccgagaa  2220
cggtccccta gggtgcctag ggacttccgg agcccgaccg gatccggaag cttctgagag  2280
cgaggggggtg gggccgaaaa tcaaaaaaag cgcggcgaaa gctaaaggcc ggcgcacgct  2340
gggcggtggt ggtccctaag ccgggccgcg gccggtgcaa tggactccac tgcctgcttg  2400
aagtccttgc tcctgactgt cagtcagtac aaagccgtga agtcagagg               2449

<210> SEQ ID NO 2
<211> LENGTH: 1522
<212> TYPE: DNA
<213> ORGANISM: Homo sapiens

<400> SEQUENCE: 2
ctcccttggc cagattttac ctaatgaaga ttctgcagca gtgagaactt gcctagagtc   60
acatcgtcaa aggtggagct agaatctgta agcaacctgg ctctctactc tttaccactg  120
ctgcatgtta ctgcatggtg cctctcattt atgtggtgaa tttcaaaagt actattttgt  180
atgtttccct tactagacag ttccctcgca gcaggggata ctacttcatc tctgttccct  240
gactggcagt ttctaaccca tgttacacgc tctataattg tttacggaat gaatgaaagc  300
ataaatgaac acacaagcta cccaaagatt tttcatgaa tgtcccaact ggttaaatca  360
tttttatctt tcagatttaa acttttataa aaacaaaac caaaacacca aacctgtctt  420
```

-continued

```
caaaaatcta gtaattcaaa aaaattcttt tgaagtgaaa aaacatgatt tctgataaac      480
gatttaatta aatggaaatg taccctattc ttacaatttc tacatcctgg tttttaaagc      540
tttattcgac gttaggaaat attaagcaaa aagctccaaa accagtaact gactcgcttc      600
attacataca catgcaataa tattaagcta tctccgattt aaaaaacgca ataatagtg        660 ccattttcgt agacatcgag aattataaaa caatcaatca tgccagagag aaacagacac      720
cttcacttac aaaaactgac gctaacgagt aacaccctcc ggagcaatac ctggcccagg      780
gtcagcagga ggtagtcttc tcgaataaat gtgacaaata ctttggtcag gcatgacta       840 atttgccaca taatgccaat aggttgactc tgagaaacta ccatccccgg gcagaagggg      900
cgggtgtagg agagatttaa aaacgaggcc cctcccaggc cgcctcaaaa tctagggccc      960
aagattcttc tcctcagagc tcctcaccgt gtctagacta ggggcaagcg accatttctc      1020
aggtagagga tgacgcacaa acgaaaaact ggccatccaa catgaaggac gaggaagcgc      1080
acgaaatcag agcgcacagc tgagtgagga atccccttc tcctaaccga ttcctctccc       1140
gagaaatcgc gagatttctc gccttcacgg gatctcaggc cgaaaacctc gcggcctctc      1200
agacgagggt gggttagcgg gggcagctcc caaccccgt cctggaccca caaatcacct       1260 cgaccctgg cccaccccgg ccgtcaccga aacggtccc ctagggtgcc tagggacttc        1320
cggagcccga ccggatccgg aagcttctga gagcgagggg gtggggccga aaatcaaaaa      1380
aagcgcggcg aaagctaaag gccggcgcac gctgggcggt ggtggtccct aagccgggcc      1440
gcggccggtg caatggactc cactgcctgc ttgaagtcct tgctcctgac tgtcagtcag      1500
tacaaagccg tgaagtcaga gg                                               1522
```

<210> SEQ ID NO 3
<211> LENGTH: 1011
<212> TYPE: DNA
<213> ORGANISM: Homo sapiens

<400> SEQUENCE: 3

```
tacaatttct acatcctggt ttttaaagct ttattcgacg ttaggaaata ttaagcaaaa      60
agctccaaaa ccagtaactg actcgcttca ttacatacac atgcaataat attaagctat     120
ctccgattta aaaaacgcaa ataatagtgc cattttcgta gacatcgaga attataaaac     180
aatcaatcat gccagagaga aacagacacc ttcacttaca aaaactgacg ctaacgagta     240
acaccctccg gagcaatacc tggcccaggg tcagcaggag gtagtcttct cgaataaatg     300
tgacaaatac tttggtcagg catgactaa tttgccacat aatgccaata ggttgactct      360
gagaaactac catccccggg cagaagsggc gggtgtagga gagatttaaa aacgaggccc     420
ctcccaggcc gcctcaaaat ctagggccca agattcttct cctcagagct cctcaccgtg     480
tctagactag gggcaagcga ccatttctca ggtagaggat gacgcacaaa cgaaaaactg     540
gccatccaac atgaaggacg aggaagcgca cgaaatcaga gcgcacagct gagtgaggaa     600 tccccttct cctaaccgat tcctctcccg agaaatcgcg agatttctcg ccttcacggg      660
atctcaggcc gaaaacctcg cggcctctca gacgagggtg ggttagcggg ggcagctccc     720 aaccccgtc ctggacccac aaatcacctc gaccctggc ccaccccggc cgtcaccgag       780
aacggtcccc tagggtgcct agggacttcc ggagcccgac cggatccgga agcttctgag     840
agcgaggggt ggggccgaa aatcaaaaaa agcgcggcga aagctaaagg ccggcgcacg      900
ctgggcggtg gtggtcccta agccgggccg cggccggtgc aatggactcc actgcctgct     960
tgaagtcctt gctcctgact gtcagtcagt acaaagccgt gaagtcagag g              1011
```

<210> SEQ ID NO 4
<211> LENGTH: 498
<212> TYPE: DNA
<213> ORGANISM: Homo sapiens

<400> SEQUENCE: 4

```
agaggatgac gcacaaacga aaaactggcc atccaacatg aaggacgagg aagcgcacga        60
aatcagagcg cacagctgag tgaggaatcc cccttctcct aaccgattcc tctcccgaga       120
aatcgcgaga tttctcgcct tcacgggatc tcaggccgaa aacctcgcgg cctctcagac       180
gagggtgggt tagcggggc agctcccaac ccccgtcctg gacccacaaa tcacctcgac        240
ccctggccca ccccggccgt caccgagaac ggtcccctag ggtgcctagg gacttccgga       300
gcccgaccgg atccggaagc ttctgagagc gagggggtgg ggccgaaaat caaaaaaagc       360
gcggcgaaag ctaaaggccg cgcacgctg gcggtggtg gtccctaagc cgggccgcgg         420
ccggtgcaat ggactccact gcctgcttga agtccttgct cctgactgtc agtcagtaca       480
aagccgtgaa gtcagagg                                                     498
```

<210> SEQ ID NO 5
<211> LENGTH: 354
<212> TYPE: DNA
<213> ORGANISM: Homo sapiens

<400> SEQUENCE: 5

```
gggatctcag gccgaaaacc tcgcggcctc tcagacgagg gtgggttagc ggggcagct        60 cccaaccccc gtcctggacc cacaaatcac ctcgacccct ggccacccc ggccgtcacc       120 gagaacggtc ccctagggtg cctagggact tccggagccc gaccggatcc ggaagcttct      180
gagagcgagg gggtgggcc gaaaatcaaa aaaagcgcgg cgaaagctaa aggccggcgc       240
acgctgggcg gtggtggtcc ctaagccggg ccgcggccgt gcaatggac tccactgcct       300 gcttgaagtc cttgctcctg actgtcagtc agtacaaagc cgtgaagtca gagg            354
```

<210> SEQ ID NO 6
<211> LENGTH: 283
<212> TYPE: DNA
<213> ORGANISM: Homo sapiens

<400> SEQUENCE: 6

```
tcctggaccc acaaatcacc tcgacccctg gccacccccg gccgtcaccg agaacggtcc        60
cctagggtgc ctagggactt ccggagcccg accggatccg gaagcttctg agagcgaggg      120
ggtggggccg aaaatcaaaa aaagcgcggc gaaagctaaa ggccggcgca cgctgggcgg      180
tggtggtccc taagccgggc cgcggccggt gcaatggact ccactgcctg cttgaagtcc      240
ttgctcctga ctgtcagtca gtacaaagcc gtgaagtcag agg                         283
```

<210> SEQ ID NO 7
<211> LENGTH: 241
<212> TYPE: DNA
<213> ORGANISM: Homo sapiens

<400> SEQUENCE: 7

```
cgtcaccgag aacggtcccc tagggtgcct agggacttcc ggagcccgac cggatccgga        60
agcttctgag agcgaggggg tggggccgaa aatcaaaaaa agcgcggcga aagctaaagg       120
ccggcgcacg ctgggcggtg gtggtcccta agccgggccg cggccggtgc aatggactcc       180
actgcctgct tgaagtcctt gctcctgact gtcagtcagt acaaagccgt gaagtcagag       240
```

```
                                                              g                                                                    241

<210> SEQ ID NO 8
<211> LENGTH: 193
<212> TYPE: DNA
<213> ORGANISM: Homo sapiens

<400> SEQUENCE: 8
accggatccg gaagcttctg agagcgaggg ggtggggccg aaaatcaaaa aaagcgcggc        60
gaaagctaaa ggccggcgca cgctgggcgg tggtggtccc taagccgggc cgcggccggt       120
gcaatggact ccactgcctg cttgaagtcc ttgctcctga ctgtcagtca gtacaaagcc       180
gtgaagtcag agg                                                          193

<210> SEQ ID NO 9
<211> LENGTH: 165
<212> TYPE: DNA
<213> ORGANISM: Homo sapiens

<400> SEQUENCE: 9
ggggtggggc cgaaaatcaa aaaagcgcg gcgaaagcta aggccggcg cacgctgggc          60 ggtggtggtc cctaagccgg gccgcggccg gtgcaatgga ctccactgcc tgcttgaagt       120
ccttgctcct gactgtcagt cagtacaaag ccgtgaagtc agagg                       165

<210> SEQ ID NO 10
<211> LENGTH: 30
<212> TYPE: DNA
<213> ORGANISM: Homo sapiens

<400> SEQUENCE: 10
gctagcaaac tggaaattaa aagcgtgagc                                         30

<210> SEQ ID NO 11
<211> LENGTH: 31
<212> TYPE: DNA
<213> ORGANISM: Homo sapiens

<400> SEQUENCE: 11
gctagcctcc cttggccaga ttttacctaa t                                       31

<210> SEQ ID NO 12
<211> LENGTH: 27
<212> TYPE: DNA
<213> ORGANISM: Homo sapiens

<400> SEQUENCE: 12
ctcgagcctc tgacttcacg gctttgt                                            27

<210> SEQ ID NO 13
<211> LENGTH: 27
<212> TYPE: DNA
<213> ORGANISM: Homo sapiens

<400> SEQUENCE: 13
ctcgagcctc tgacttcacg gctttgt                                            27

<210> SEQ ID NO 14
<211> LENGTH: 35
<212> TYPE: DNA
<213> ORGANISM: Homo sapiens
```

<400> SEQUENCE: 14
gctagctaca atttctacat cctggttttt aaagc					35

<210> SEQ ID NO 15
<211> LENGTH: 27
<212> TYPE: DNA
<213> ORGANISM: Homo sapiens

<400> SEQUENCE: 15
ctcgagcctc tgacttcacg gctttgt					27

<210> SEQ ID NO 16
<211> LENGTH: 30
<212> TYPE: DNA
<213> ORGANISM: Homo sapiens

<400> SEQUENCE: 16
gctagcagag gatgacgcac aaacgaaaaa					30

<210> SEQ ID NO 17
<211> LENGTH: 27
<212> TYPE: DNA
<213> ORGANISM: Homo sapiens

<400> SEQUENCE: 17
ctcgagcctc tgacttcacg gctttgt					27

<210> SEQ ID NO 18
<211> LENGTH: 24
<212> TYPE: DNA
<213> ORGANISM: Homo sapiens

<400> SEQUENCE: 18
gctagcggga tctcaggccg aaaa					24

<210> SEQ ID NO 19
<211> LENGTH: 27
<212> TYPE: DNA
<213> ORGANISM: Homo sapiens

<400> SEQUENCE: 19
ctcgagcctc tgacttcacg gctttgt					27

<210> SEQ ID NO 20
<211> LENGTH: 27
<212> TYPE: DNA
<213> ORGANISM: Homo sapiens

<400> SEQUENCE: 20
gctagctcct ggacccacaa atcacct					27

<210> SEQ ID NO 21
<211> LENGTH: 27
<212> TYPE: DNA
<213> ORGANISM: Homo sapiens

<400> SEQUENCE: 21
ctcgagcctc tgacttcacg gctttgt					27

<210> SEQ ID NO 22
<211> LENGTH: 23
<212> TYPE: DNA
<213> ORGANISM: Homo sapiens

```
<400> SEQUENCE: 22
gctagccgtc accgagaacg gtc                                          23

<210> SEQ ID NO 23
<211> LENGTH: 27
<212> TYPE: DNA
<213> ORGANISM: Homo sapiens

<400> SEQUENCE: 23
ctcgagcctc tgacttcacg gctttgt                                      27

<210> SEQ ID NO 24
<211> LENGTH: 23
<212> TYPE: DNA
<213> ORGANISM: Homo sapiens

<400> SEQUENCE: 24
gctagcaccg gatccggaag ctt                                          23

<210> SEQ ID NO 25
<211> LENGTH: 27
<212> TYPE: DNA
<213> ORGANISM: Homo sapiens

<400> SEQUENCE: 25
ctcgagcctc tgacttcacg gctttgt                                      27

<210> SEQ ID NO 26
<211> LENGTH: 27
<212> TYPE: DNA
<213> ORGANISM: Homo sapiens

<400> SEQUENCE: 26
gctagcgggg tggggccgaa aatcaaa                                      27

<210> SEQ ID NO 27
<211> LENGTH: 27
<212> TYPE: DNA
<213> ORGANISM: Homo sapiens

<400> SEQUENCE: 27
ctcgagcctc tgacttcacg gctttgt                                      27

<210> SEQ ID NO 28
<211> LENGTH: 20
<212> TYPE: DNA
<213> ORGANISM: Homo sapiens

<400> SEQUENCE: 28
ctagcaaaat aggctgtccc                                              20

<210> SEQ ID NO 29
<211> LENGTH: 20
<212> TYPE: DNA
<213> ORGANISM: Homo sapiens

<400> SEQUENCE: 29
gacgatagtc atgccccgcg                                              20

<210> SEQ ID NO 30
<211> LENGTH: 19
<212> TYPE: RNA
<213> ORGANISM: Homo sapiens
```

-continued

```
<400> SEQUENCE: 30
cagaaugacu acuuugcua                                                19

<210> SEQ ID NO 31
<211> LENGTH: 19
<212> TYPE: RNA
<213> ORGANISM: Homo sapiens

<400> SEQUENCE: 31
gaaaugaugu cucaagcau                                                19

<210> SEQ ID NO 32
<211> LENGTH: 19
<212> TYPE: RNA
<213> ORGANISM: Homo sapiens

<400> SEQUENCE: 32
gcagcagccg gaacgagua                                                19

<210> SEQ ID NO 33
<211> LENGTH: 19
<212> TYPE: RNA
<213> ORGANISM: Homo sapiens

<400> SEQUENCE: 33
cggaagagcu uaaugugga                                                19

<210> SEQ ID NO 34
<211> LENGTH: 19
<212> TYPE: DNA
<213> ORGANISM: Homo sapiens

<400> SEQUENCE: 34
cagaatgact actttgcta                                                19

<210> SEQ ID NO 35
<211> LENGTH: 19
<212> TYPE: DNA
<213> ORGANISM: Homo sapiens

<400> SEQUENCE: 35
cagaatgact actttgcta                                                19

<210> SEQ ID NO 36
<211> LENGTH: 19
<212> TYPE: DNA
<213> ORGANISM: Homo sapiens

<400> SEQUENCE: 36
gaaatgatgt ctcaagcat                                                19

<210> SEQ ID NO 37
<211> LENGTH: 19
<212> TYPE: DNA
<213> ORGANISM: Homo sapiens

<400> SEQUENCE: 37
gaaatgatgt ctcaagcat                                                19

<210> SEQ ID NO 38
<211> LENGTH: 19
<212> TYPE: DNA
<213> ORGANISM: Homo sapiens
```

```
<400> SEQUENCE: 38
gcagcagccg gaacgagta                                               19

<210> SEQ ID NO 39
<211> LENGTH: 19
<212> TYPE: DNA
<213> ORGANISM: Homo sapiens

<400> SEQUENCE: 39
gcagcagccg gaacgagta                                               19

<210> SEQ ID NO 40
<211> LENGTH: 19
<212> TYPE: DNA
<213> ORGANISM: Homo sapiens

<400> SEQUENCE: 40
cggaagagct taatgtgga                                               19

<210> SEQ ID NO 41
<211> LENGTH: 19
<212> TYPE: DNA
<213> ORGANISM: Homo sapiens

<400> SEQUENCE: 41
cggaagagct taatgtgga                                               19

<210> SEQ ID NO 42
<211> LENGTH: 124
<212> TYPE: DNA
<213> ORGANISM: Homo sapiens

<400> SEQUENCE: 42
ggacttccgg agcccgaccg gatccggaag cttctgagag cgaggggtg gggccgaaaa   60 tcaaaaaaag cgcggcgaaa gctaaaggcc ggcgcacgct gggcggtggt ggtccctaag 120
ccgg                                                              124

<210> SEQ ID NO 43
<211> LENGTH: 279
<212> TYPE: DNA
<213> ORGANISM: Homo sapiens

<400> SEQUENCE: 43
aaactggaaa ttaaaagcgt gagccactgc tcctggcctc ctgctccttt tcttcccttt   60
ttgaggccta aaagtatgga ttggtgtttc tcaaattagg atatgcaagt atctctgatt  120
aaaaatgtca agactatca cagctagaaa cgatccctct tactaaactt acaacatcaa  180
ttttggtgaa gattttttga gaaagacatt tgatattaat tacagaagag aatacaaaat  240
ttgtatgact gcttaagtca aaatccaaca aagatggca                        279

<210> SEQ ID NO 44
<211> LENGTH: 20
<212> TYPE: DNA
<213> ORGANISM: Homo sapiens

<400> SEQUENCE: 44
ggacttccgg agcccgaccg                                              20
```

<210> SEQ ID NO 45
<211> LENGTH: 21
<212> TYPE: DNA
<213> ORGANISM: Homo sapiens

<400> SEQUENCE: 45
ccggcttagg gaccaccacc g                                              21

<210> SEQ ID NO 46
<211> LENGTH: 24
<212> TYPE: DNA
<213> ORGANISM: Homo sapiens

<400> SEQUENCE: 46
aaactggaaa ttaaaagcgt gagc                                           24

<210> SEQ ID NO 47
<211> LENGTH: 26
<212> TYPE: DNA
<213> ORGANISM: Homo sapiens

<400> SEQUENCE: 47
tgccatcttt gttggatttt gactta                                         26

<210> SEQ ID NO 48
<211> LENGTH: 19
<212> TYPE: DNA
<213> ORGANISM: Homo sapiens

<400> SEQUENCE: 48
tgcctgcttg aagtccttg                                                 19

<210> SEQ ID NO 49
<211> LENGTH: 21
<212> TYPE: DNA
<213> ORGANISM: Homo sapiens

<400> SEQUENCE: 49
tagtcgtgtg agtttctgtc c                                              21

<210> SEQ ID NO 50
<211> LENGTH: 20
<212> TYPE: DNA
<213> ORGANISM: Homo sapiens

<400> SEQUENCE: 50
tgggctacac tgagcaccag                                                20

<210> SEQ ID NO 51
<211> LENGTH: 20
<212> TYPE: DNA
<213> ORGANISM: Homo sapiens

<400> SEQUENCE: 51
gggtgtcgct gttgaagtca                                                20

<210> SEQ ID NO 52
<211> LENGTH: 25
<212> TYPE: DNA
<213> ORGANISM: Homo sapiens

<400> SEQUENCE: 52
atgagctact ttgtggattc tgctg                                          25

```
<210> SEQ ID NO 53
<211> LENGTH: 30
<212> TYPE: DNA
<213> ORGANISM: Homo sapiens

<400> SEQUENCE: 53
tcactcgtcg gcatctggct tgacgtccag                                    30

<210> SEQ ID NO 54
<211> LENGTH: 15
<212> TYPE: DNA
<213> ORGANISM: Homo sapiens

<400> SEQUENCE: 54
atggacccat ctgtg                                                    15

<210> SEQ ID NO 55
<211> LENGTH: 30
<212> TYPE: DNA
<213> ORGANISM: Homo sapiens

<400> SEQUENCE: 55
tcatggcttc tggggccctg gggagagcac                                    30

<210> SEQ ID NO 56
<211> LENGTH: 33
<212> TYPE: DNA
<213> ORGANISM: Homo sapiens

<400> SEQUENCE: 56
ataacttccg gagcccgacc ggatccggaa gct                                33

<210> SEQ ID NO 57
<211> LENGTH: 33
<212> TYPE: DNA
<213> ORGANISM: Homo sapiens

<400> SEQUENCE: 57
gggacggttg gagcccgacc ggatccggaa gct                                33

<210> SEQ ID NO 58
<211> LENGTH: 25
<212> TYPE: DNA
<213> ORGANISM: Homo sapiens

<400> SEQUENCE: 58
gggaccccga ccggatccgg aagct                                         25

<210> SEQ ID NO 59
<211> LENGTH: 33
<212> TYPE: DNA
<213> ORGANISM: Homo sapiens

<400> SEQUENCE: 59
gggacttccg gagtttgacc ggatccggaa gct                                33

<210> SEQ ID NO 60
<211> LENGTH: 25
<212> TYPE: DNA
<213> ORGANISM: Homo sapiens

<400> SEQUENCE: 60
gggacttccg gagcccgacc ggatt                                         25
```

-continued

```
<210> SEQ ID NO 61
<211> LENGTH: 33
<212> TYPE: DNA
<213> ORGANISM: Homo sapiens

<400> SEQUENCE: 61
gggacttccg gagcccgacc ggattttttt ttt                                    33

<210> SEQ ID NO 62
<211> LENGTH: 19
<212> TYPE: RNA
<213> ORGANISM: Artificial
<220> FEATURE:
<223> OTHER INFORMATION: siRNA

<400> SEQUENCE: 62
gguuggacuc ugaauuuug                                                    19

<210> SEQ ID NO 63
<211> LENGTH: 18
<212> TYPE: RNA
<213> ORGANISM: Artificial
<220> FEATURE:
<223> OTHER INFORMATION: siRNA

<400> SEQUENCE: 63
ccccaagguu aaauacaa                                                     18

<210> SEQ ID NO 64
<211> LENGTH: 19
<212> TYPE: RNA
<213> ORGANISM: Artificial
<220> FEATURE:
<223> OTHER INFORMATION: siRNA

<400> SEQUENCE: 64
gcgguuuauu uauuuauuu                                                    19

<210> SEQ ID NO 65
<211> LENGTH: 19
<212> TYPE: RNA
<213> ORGANISM: Artificial
<220> FEATURE:
<223> OTHER INFORMATION: siRNA

<400> SEQUENCE: 65
cugccauuuu gauaguaua                                                    19

<210> SEQ ID NO 66
<211> LENGTH: 32
<212> TYPE: DNA
<213> ORGANISM: Homo sapiens

<400> SEQUENCE: 66
gacttccgga gcccgaccgg atccggaagc tt                                     32

<210> SEQ ID NO 67
<211> LENGTH: 32
<212> TYPE: DNA
<213> ORGANISM: Homo sapiens

<400> SEQUENCE: 67
gaaaatttaa gcccgaccgg ataaatttac tt                                     32
```

```
<210> SEQ ID NO 68
<211> LENGTH: 21
<212> TYPE: DNA
<213> ORGANISM: Homo sapiens

<400> SEQUENCE: 68
gatctcgagc aggaagttcg a                                         21

<210> SEQ ID NO 69
<211> LENGTH: 30
<212> TYPE: DNA
<213> ORGANISM: Homo sapiens

<400> SEQUENCE: 69
tttgcaaaat gcaggaattg ttttcacagt                                30

<210> SEQ ID NO 70
<211> LENGTH: 33
<212> TYPE: DNA
<213> ORGANISM: Homo sapiens

<400> SEQUENCE: 70
gggacttccg gagcccgacc ggatccggaa gct                            33
```